(12) United States Patent
Wood et al.

(10) Patent No.: US 9,320,288 B2
(45) Date of Patent: Apr. 26, 2016

(54) CONTROLLED RELEASE COMPOSITIONS AND METHODS OF USING

(71) Applicants: Kimberly-Clark Worldwide, Inc., Neenah, WI (US); Cellresin Technologies, LLC, West Bloomington, MN (US)

(72) Inventors: Willard E. Wood, Arden Hills, MN (US); Ali Yahiaoui, Roswell, GA (US)

(73) Assignees: Cellresin Technologies, LLC, West Bloomington, MN (US); Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 14/094,416

(22) Filed: Dec. 2, 2013

(65) Prior Publication Data

US 2014/0154370 A1 Jun. 5, 2014

Related U.S. Application Data

(63) Continuation of application No. PCT/US2013/072124, filed on Nov. 27, 2013.

(60) Provisional application No. 61/732,103, filed on Nov. 30, 2012.

(51) Int. Cl.
*B29C 65/00* (2006.01)
*B32B 37/00* (2006.01)
(Continued)

(52) U.S. Cl.
CPC ............... *A23B 7/154* (2013.01); *B41M 3/006* (2013.01); *Y10T 156/10* (2015.01)

(58) Field of Classification Search
CPC ........ B29C 65/00; B29C 65/02; B29C 65/48;
B32B 27/00; B32B 27/28; B32B 27/30;
B32B 27/32; B32B 27/34; B32B 27/36;
B32B 27/40; B32B 27/42; B32B 37/00;
B32B 37/10; B32B 37/08; B32B 37/12;
A01N 25/00; A01N 25/10; A01N 25/08;
A01N 25/26; A01N 25/28; A01N 27/00
See application file for complete search history.

(56) References Cited

U.S. PATENT DOCUMENTS 3,493,362 A 2/1970 Ferm
3,661,549 A 5/1972 Freytag et al.
(Continued)

FOREIGN PATENT DOCUMENTS

AU 2011268471 B1 3/2012
CA 2011748 A1 9/1991
(Continued)

OTHER PUBLICATIONS

Office Action dated Jan. 6, 2015 in connection with Japanese Patent Application No. 2014-502539; English translation also enclosed.
(Continued)

*Primary Examiner* — Michael N Orlando
*Assistant Examiner* — Matthew Hoover
(74) *Attorney, Agent, or Firm* — Dorsey & Whitney LLP

(57) ABSTRACT

Cyclodextrin compositions, including a hydrophobic carrier and a cyclodextrin complex, are formed and disposed on a variety of substrates using conditions that avoid substantial loss of the complexed compound from the cyclodextrin complex, even where the complexed compound is a gas a common ambient temperatures (e.g. 20° C.). Flexographic printing is particularly useful for disposing the cyclodextrin compositions on one or more substrates. Substrates treated with the cyclodextrin complexes are useful for subsequent release of the complexed compound.

5 Claims, 4 Drawing Sheets

(51) Int. Cl.
*A23B 7/154* (2006.01)
*B41M 3/00* (2006.01)

(56) References Cited

U.S. PATENT DOCUMENTS

| | | | |
|---|---|---|---|
| 3,676,102 A | 7/1972 | Clark et al. | |
| 3,810,749 A | 5/1974 | Young | |
| 3,840,448 A | 10/1974 | Osborn et al. | |
| 3,879,188 A | 4/1975 | Fritz et al. | |
| 3,885,950 A | 5/1975 | Ehrig et al. | |
| 3,940,667 A | 2/1976 | Pearce | |
| 3,943,103 A | 3/1976 | Borden et al. | |
| 4,162,165 A * | 7/1979 | Schwab | 106/31.16 |
| 4,181,752 A | 1/1980 | Martens et al. | |
| 4,356,115 A | 10/1982 | Shibanai et al. | |
| 4,432,802 A | 2/1984 | Harata et al. | |
| 4,438,106 A | 3/1984 | Wagu et al. | |
| 4,547,572 A | 10/1985 | Fenyvesi et al. | |
| 4,575,548 A | 3/1986 | Ueda et al. | |
| 4,636,343 A | 1/1987 | Shibanai | |
| 4,675,395 A | 6/1987 | Fukazawa et al. | |
| 4,677,177 A | 6/1987 | Shibanai et al. | |
| 4,681,934 A | 7/1987 | Shibanai et al. | |
| 4,711,936 A | 12/1987 | Shibanai et al. | |
| 4,722,815 A | 2/1988 | Shibanai | |
| 4,725,633 A | 2/1988 | Shibanai | |
| 4,725,657 A | 2/1988 | Shibanai | |
| 4,728,510 A | 3/1988 | Shibanai et al. | |
| 4,732,758 A | 3/1988 | Hurion et al. | |
| 4,732,759 A | 3/1988 | Shibanai et al. | |
| 4,769,242 A | 9/1988 | Shibanai | |
| 4,772,291 A | 9/1988 | Shibanai et al. | |
| 4,833,674 A | 5/1989 | Takai et al. | |
| 4,834,985 A | 5/1989 | Elger et al. | |
| 4,847,151 A | 7/1989 | Ichiro | |
| 4,871,541 A | 10/1989 | Shibanai | |
| 4,883,674 A | 11/1989 | Fan | |
| 5,070,081 A | 12/1991 | Majid et al. | |
| 5,078,920 A | 1/1992 | Maza | |
| 5,100,462 A | 3/1992 | Sisler et al. | |
| 5,183,655 A | 2/1993 | Stanislowski et al. | |
| 5,360,899 A | 11/1994 | Nussstein et al. | |
| 5,474,698 A | 12/1995 | Rolando et al. | |
| 5,505,969 A | 4/1996 | Wood et al. | |
| 5,518,988 A | 5/1996 | Sisler et al. | |
| 5,723,714 A | 3/1998 | Binger | |
| 5,730,311 A | 3/1998 | Curtis | |
| 5,760,129 A | 6/1998 | Lau | |
| 5,776,842 A | 7/1998 | Wood et al. | |
| 5,832,699 A | 11/1998 | Zobel | |
| 5,985,772 A | 11/1999 | Wood et al. | |
| 6,017,849 A | 1/2000 | Daly et al. | |
| 6,092,761 A | 7/2000 | Mushaben | |
| 6,162,533 A | 12/2000 | Onozawa et al. | |
| 6,194,350 B1 | 2/2001 | Sisler | |
| 6,206,947 B1 | 3/2001 | Evans et al. | |
| 6,218,013 B1 | 4/2001 | Wood et al. | |
| 6,232,365 B1 | 5/2001 | Weiss et al. | |
| 6,271,127 B1 | 8/2001 | Liu et al. | |
| 6,296,923 B1 | 10/2001 | Zobel | |
| 6,313,068 B1 | 11/2001 | Daly et al. | |
| 6,358,670 B1 | 3/2002 | Wong et al. | |
| 6,365,549 B2 | 4/2002 | Sisler | |
| 6,426,319 B1 | 7/2002 | Kostansek | |
| 6,444,619 B1 | 9/2002 | Kostansek | |
| 6,451,065 B2 | 9/2002 | Trinh et al. | |
| 6,452,060 B2 | 9/2002 | Jacobson | |
| 6,548,132 B1 | 4/2003 | Clarke et al. | |
| 6,548,448 B2 * | 4/2003 | Kostansek | 504/193 |
| 6,613,703 B1 | 9/2003 | Yahiaoui et al. | |
| 6,709,746 B2 | 3/2004 | Wood et al. | |
| 6,720,476 B2 | 4/2004 | Clendennen et al. | |
| 6,739,110 B2 * | 5/2004 | Ogden et al. | 53/411 |
| 6,762,153 B2 | 7/2004 | Kostansek et al. | |
| 6,766,612 B1 | 7/2004 | Liu | |
| 6,770,600 B1 | 8/2004 | Lamola et al. | |
| 6,831,116 B2 | 12/2004 | Bitler et al. | |
| 6,852,904 B2 | 2/2005 | Sun et al. | |
| 6,953,540 B2 | 10/2005 | Chong et al. | |
| 6,987,099 B2 | 1/2006 | Trinh et al. | |
| 7,001,661 B2 | 2/2006 | Beaverson et al. | |
| 7,019,073 B2 | 3/2006 | Etherton et al. | |
| 7,041,625 B2 | 5/2006 | Jacobson et al. | |
| 7,157,411 B2 | 1/2007 | Rohde et al. | |
| 7,166,671 B2 | 1/2007 | Wood et al. | |
| 7,169,451 B2 | 1/2007 | Clarke et al. | |
| 7,182,941 B2 | 2/2007 | Trinh et al. | |
| 7,365,123 B2 | 4/2008 | Wood et al. | |
| 7,531,471 B2 | 5/2009 | Quincy, III | |
| 7,547,443 B2 | 6/2009 | Krzysik et al. | |
| 7,549,396 B2 | 6/2009 | Hurwitz et al. | |
| 7,569,160 B2 | 8/2009 | Oldenzijl et al. | |
| 7,601,374 B2 | 10/2009 | Clarke | |
| 7,629,042 B2 | 12/2009 | Jones et al. | |
| 7,637,054 B2 | 12/2009 | Alfrey et al. | |
| 7,713,561 B2 | 5/2010 | Popa et al. | |
| 7,758,885 B2 | 7/2010 | Myhra | |
| 7,799,885 B2 | 9/2010 | Shustack et al. | |
| 7,943,549 B2 | 5/2011 | Pierce et al. | |
| 7,997,026 B2 | 8/2011 | Webster et al. | |
| 8,093,430 B2 | 1/2012 | Sisler | |
| 8,168,860 B2 | 5/2012 | Rosichan et al. | |
| 8,247,459 B2 | 8/2012 | Kostansek | |
| 8,314,051 B2 | 11/2012 | Yoo | |
| 8,414,989 B2 | 4/2013 | Wood et al. | |
| 8,461,086 B2 | 6/2013 | Chang et al. | |
| 8,481,127 B2 | 7/2013 | Wood et al. | |
| 2002/0007055 A1 | 1/2002 | Uchiyama et al. | |
| 2002/0012759 A1 | 1/2002 | Asayama et al. | |
| 2002/0043730 A1 | 4/2002 | Chong et al. | |
| 2002/0164444 A1 * | 11/2002 | Hunt et al. | 428/36.7 |
| 2002/0198107 A1 | 12/2002 | Kostansek | |
| 2005/0043482 A1 | 2/2005 | Etherton et al. | |
| 2005/0260907 A1 | 11/2005 | Chang et al. | |
| 2005/0261131 A1 | 11/2005 | Basel et al. | |
| 2005/0261426 A1 | 11/2005 | Wood et al. | |
| 2006/0164822 A1 | 7/2006 | Kobayashi et al. | |
| 2007/0105722 A1 | 5/2007 | Basel et al. | |
| 2009/0088323 A1 | 4/2009 | Basel et al. | |
| 2009/0220739 A1 | 9/2009 | Chougule | |
| 2010/0144533 A1 | 6/2010 | Baier et al. | |
| 2011/0033540 A1 | 2/2011 | Daniloff et al. | |
| 2011/0143004 A1 | 6/2011 | Wood et al. | |
| 2011/0253562 A1 | 10/2011 | Machado | |
| 2012/0004108 A1 | 1/2012 | Zhen | |
| 2012/0107459 A1 | 5/2012 | Wood et al. | |
| 2012/0258220 A1 | 10/2012 | Jacobson | |
| 2013/0029058 A1 | 1/2013 | Wood et al. | |
| 2014/0011679 A1 | 1/2014 | Mir | |

FOREIGN PATENT DOCUMENTS

| | | |
|---|---|---|
| CA | 2692211 A1 | 8/2010 |
| CN | 1371603 A | 10/2002 |
| CN | 1457636 A | 11/2003 |
| CN | 1703955 A | 12/2005 |
| CN | 101104665 A | 1/2008 |
| CN | 101297659 A | 11/2008 |
| CN | 201501603 U | 6/2010 |
| CN | 101990937 A | 3/2011 |
| CN | 102047946 A | 5/2011 |
| CN | 102119719 A | 7/2011 |
| CN | 102532611 A | 7/2012 |
| DE | 4035378 A1 | 5/1992 |
| EP | 0180468 A2 | 5/1986 |
| EP | 0514578 A1 | 11/1992 |
| EP | 1236397 A2 | 9/2002 |
| EP | 1559746 A1 | 8/2005 |
| EP | 1593306 A2 | 11/2005 |
| EP | 2389814 A1 | 11/2011 |
| EP | 2508071 A1 | 10/2012 |
| GB | 1119545 A | 7/1968 |
| GB | 2492284 A | 12/2012 |
| GB | 2491424 B | 4/2013 |

(56) References Cited

FOREIGN PATENT DOCUMENTS

| | | |
|---|---|---|
| JP | 8-100027 A | 4/1996 |
| JP | 2002281894 A | 10/2002 |
| JP | 2002-356401 A | 12/2002 |
| JP | 2007-256773 A | 10/2007 |
| JP | 2012219096 A | 11/2012 |
| NZ | 514235 | 7/2002 |
| NZ | 514236 | 1/2003 |
| NZ | 521818 | 3/2004 |
| NZ | 524289 | 7/2004 |
| NZ | 539684 | 12/2006 |
| NZ | 551211 | 12/2008 |
| NZ | 554976 | 3/2009 |
| NZ | 563094 | 4/2009 |
| NZ | 568774 | 12/2009 |
| NZ | 578429 | 12/2011 |
| TW | 201311803 A | 3/2013 |
| WO | WO8605798 A1 | 10/1986 |
| WO | WO0113968 A1 | 3/2001 |
| WO | WO 02/20668 A2 | 3/2002 |
| WO | WO2006046254 A1 | 5/2006 |
| WO | WO2006072180 A1 | 7/2006 |
| WO | WO2008089140 A1 | 7/2008 |
| WO | WO2011081877 A1 | 7/2011 |
| WO | WO 2011109144 A1 * | 9/2011 |
| WO | WO2012134539 A1 | 10/2012 |

OTHER PUBLICATIONS

First Examination Report dated Feb. 19, 2015 in connection with related New Zealand Application No. 704723, 1 pg.
Office Action dated Feb. 10, 2015 in connection with Colombian Patent Application No. 13-252.771.
International Preliminary Report on Patentability dated Mar. 9, 2015 in connection with International Patent Application No. PCT/US2013/072124.
The First Examination Report dated Jun. 6, 2014 in related New Zealand Application No. 616943.
Aug. 26, 2014 Office Action in Japanese Application No. 2012-544678. Translation included.
Aug. 26, 2014 Office Action in European Application No. 11785170.9.
Sep. 11, 2014 Office Action in Korean Application No. 10-2013-7028386. Translation included.
Sep. 12, 2014 Examination Report in Canadian Application No. 2,831,213.
Oct. 5, 2014 Translation of Notification of Defects in Israeli Application No. 228558.
Oct. 27, 2014 Office Action in Russian Application No. 2012129253. Translation included.
Nov. 5, 2014 Final Office Action in U.S. Appl. No. 12/967,226.
Maatz, Gero et al. "Cyclodextrin-induced host-guest effects of classically prepared poly(NIPAM) bearing azo-dye end groups" Beilstein Journal of Organic Chemistry. 2012, 8, 1929-1935.
Regiert, Marlies et al. "Light-Stable Vitamin E by Inclusion in y-Cyclodextrin" Sun Screens & UV Protection, Cosmetic Science Technology, 2006, p. 95.
Notice of Allowance dated May 14, 2013 in U.S. Appl. No. 13/574,287.
First Office Action dated May 29, 2013 in Chinese Application No. 201080060634.6.
Official Action mailed Nov. 20, 2013 in Mexican Application No. MX/a/2012/006797.
Official Action mailed Feb. 7, 2014 in Mexican Application No. MX/a/2012/006797.
First Office Action dated Jun. 5, 2014 in Chinese Application No. 2011104316743.
Second Office Action dated Jan. 3, 2014 in Chinese Application No. 201080060634.6.
Notice of Acceptance dated Aug. 14, 2013 in Australian Application No. 2010337146.
Office Action dated Aug. 15, 2013 in U.S. Appl. No. 13/896,803.

First Examination Report dated Apr. 2, 2014 in Australian Application No. 2013302242.
Neoh, Tze Loon et al. "Dissociation characteristics of the inclusion complex of cyclomaltohexaose (a-cyclodextrin) with 1-methylcyclopropene in response to stepwise rising relative humidity," Carbohydrate Research, 345 (2010) pp. 2085-2089.
Olabisi, Olagoke et al. "Pressure-Volume-Temperature Studies of Amorphous and Crystallizable Polymers. I. Experimental," Macromolecules 1975, 8, pp. 206-210.
Orellana, Stephanie "Ninesigma—Request #50882-1—Entrapping Gases for Agricultural Formulations," NineSigma, Inc. www.ninesigma.com (2009) 2 pgs.
"Paraffin wax," http://www.chemicalbook.com/ChemicalProductProperty_EN_CB2854418.htm (2010) 2 pgs.
"Petrolatum," Pharmaceutical Excipients, London, Pharmaceutical Press, Electronic Version, 2006 <http://www.medicinescomplete.com/mc/excipients/current/1000304196.htm> 5 pages.
Pirrung, Michael "A new idea for how anti-aging products delay ripening of fruit and wilting of flowers," www.physorg.com/news128959515.html (May 2, 2008) 2 pgs.
"PMMA (Acrylic)," PMMA Processing Guide, http://www.fastheatuk.com/mdb/pmma.html, 1 pg.
Ellis, Bryan et al. "Poly(methyl methacrylate), General," Polymers A Property Database 2nd Ed., CRC Press 2009 by Taylor and Francis Group, Boca Raton, FL pp. 726-735.
"Regulatory Note REG2004-07," Pest Management Regulator agency, 2004. 1-Methylcyclopropene, Regulatory note REG Jul. 2004, PMRA, Health Canada, Ottawa, Ont. pp. 1-56.
Reid, Michael S. "Use of 1-Methylcyclopropene in Ornamentals: Carnations as a Model System for Understanding Mode of Action," HortScience, vol. 43 (1) Feb. 2008, pp. 95-98.
Shkolnik, S. et al. "Radiation-Induced Grafting of Sulfonates on Polyethylene," Journal of Applied Polymer Science, vol. 27, (1982) pp. 2189-2196.
Sisler, Edward C. et al. "Competition of unsaturated compounds with ethylene for binding and action in plants," Plant Growth Regulation, 9, (1988) pp. 181-191.
Sisler, Edward C. et al. "Competition of cyclooctenes and cyclooctadienes for ethylene binding and activity in plants," Plant Growth Regulation, 9 (1990) pp. 157-164.
Sisler, Edward C. et al. "Inhibitors of ethylene responses in plants at the receptor level: Recent developments," Physiologia Plantarum, 100 (1997) pp. 577-582.
Sisler, Edward C. et al. "Compounds controlling the ethylene receptor," Bot. Bull. Acad. Sin., 40 (1999) 40: 1_7 <http://ejournal.sinica.edu.tw/bbas/content/1999/1/bot41-01.html> 13 pages.
van Velzen, E.U. Thoden "Packaging for fresh convenience food," Agrotechnology & Food Sciences Group—Wageningenur, (2008) 30 pgs.
"Fresh as the day it was harvested—luscious fruit thanks to cyclodextrins," Wacker Chemie AG, www.wacker.com, No. 5 (May 2009) 9 pgs.
Watkins, Chris B. "The use of 1-methylcyclopropene (1-MCP) on fruits and vegetables," Biotechnology Advances, 24 (2006) pp. 389-409.
Watkins, Christopher B. "Overview of 1-Methylcyclopropene Trials and Uses for Edible Horticultural Crops," 2008, 19 pgs.
Watkins, Chris B. et al. "A summary of physiological processes or disorders in fruits, vegetables and ornamental products that are delayed or decreased, increased, or unaffected by application of 1-methylcyclopropene (1-MCP)," 2005, 20 pgs.
Utto, Weerawate. "Mathamatical Modelling of Active Packaging Systems for Horticultural Products," Thesis, Massey University, New Zealand, 2008, 363 pgs.
Wooster, Jeffrey J. "Extending the Shelf-life of Fresh-cut Produce (Including the Many Advantages of AFFINITYTM Polyolefin Plastomers)," The Dow Chemical Company, 2010, 16 pgs.
Zhao, Xiao-Bin et al. "Synthesis and characterization of polymer-immobilized B-cyclodextrin with an inclusion recognition functionality," Elsevier Science B.V. Reactive Polymers 24 (1994) pp. 9-16.
Office Action dated Nov. 27, 2014 in Canadian Application No. 2,867,732.

(56) References Cited

OTHER PUBLICATIONS

Office Action mailed Nov. 2, 2010 in Canadian Patent Application No. 2,692,211 (2 pages).
Office Action mailed Feb. 9, 2011 in Canadian Patent Application No. 2,692,211 (1 page).
International Preliminary Report on Patentability mailed Apr. 28, 2011 in International Application No. PCT/US2010/060067.
Combined Search and Examination Report mailed Jan. 13, 2012 in United Kingdom Application No. GB1119545.0.
International Search Report and Written Opinion mailed Jan. 30, 2012 in International Application No. PCT/US2011/057017.
Examination Report mailed Feb. 6, 2012 in Australian Application No. AU2011268471.
Examination Report mailed Apr. 4, 2012 in United Kingdom Application No. GB1119545.0.
Non-Final Office Action mailed Apr. 27, 2012 in U.S. Appl. No. 13/287,944.
International Preliminary Report on Patentability mailed Jun. 28, 2012 in International Application No. PCT/US2010/060067.
Examination Report mailed Sep. 11, 2012 in United Kingdom Application No. GB1119545.0.
Combined Search and Examination Report mailed Oct. 23, 2012 in United Kingdom Application No. GB1218077.4.
Final Office Action mailed Nov. 8, 2012 in U.S. Appl. No. 13/287,944.
Examination Report mailed Nov. 9, 2012 in Australian Application No. AU2010337146.
Non-Final Office Action mailed Nov. 26, 2012 in U.S. Appl. No. 12/967,226.
Notice of Allowance mailed Feb. 8, 2013 in U.S. Appl. No. 13/287,944.
Examination Report mailed Feb. 19, 2013 in Australian Application No. AU2010337146.
Examination Report mailed Mar. 22, 2013 in Australian Application No. AU2012203412.
Final Office Action mailed Apr. 26, 2013 in U.S. Appl. No. 12/967,226.
"AFFINIMM kc 8852G, Polyolefin Plastomer," Form No. 400-00050072en, REv: Jun. 3, 2009, The Dow Chemical Company, www.dowplastics.com (2009).
"AFFINIMM PF 1140G, Polyolefin Plastomer," Form No. 400-00071417en, Rev: Jun. 3, 2009, The Dow Chemical Company, www.dowplastics.com (2009).
Ambaw, Alemayehu et al. "Modeling of Diffusion-Adsorption Kinetics of 1-Methylcyclopropene (1-MCP) in Apple Fruit and Non-Target Materials in Storage Rooms," (2010) 5 pgs.
Amiel, Catherine. "Cyclodextrin polymers and drug delivery," Systemes Polymeres Complexes, ICMPE J. Drug Del. Sci. Tech. (2004) 21 pgs.
"Basell—Polybutene-1 PB 0300M-Polybutene-1," http://basell.com/portal/binary/com.vignette.vps.basell.productgrade.ProductGradeFileDisplay?id27d684b40c337010VgnVC . . . (Jul. 18, 2006) 2 pgs.
Blankenship, Sylvia M. et al. "1-Methylcyclopropene: a review," Postharvest Biology and Technology, 28 (2003) 25 pgs.
Burg, Stanley P. et al. "Molecular Requirements for the Biological Activity of Ethylene," Plant Physiolo. 42, pp. 144-152 (1967).
Chanda, Manas et al. "Plastics Technology Handbook," 4th Ed., CRC Press, p. 1-34 (1 page).
Cheng, Jianjun et al. "Synthesis of Linear, B-Cyclodextrin-Based Polymers and Their Camptothecin Conjugates," Bioconjugate Chem. 14 (2003) pp. 1007-1017.
DeEll, Jennifer R. et al. "1-Methylcyclopropene Influences 'Empire' and 'Delicious' Apple Quality during Long-term Commercial Storage," HortTechnology, Jan.-Mar. 2007, 17(1) pp. 46-51.
Denter, U. et al. "Surface modification of synthetic and natural fibres by fixation of cyclodextrin derivatives," Journal of Inclusion Phenomena an dMolecular Recognition in Chemistry 25, pp. 197-202, 1996.

"DuPontTM FusabondR P MD353D," DuPont Packaging & Industrial Polymers, http://www.dupont.com (Jun. 2005) 2 pgs.
"Conclusion regarding the peer review of the pesticide risk assessment of the active substance 1-methylcyclopropene," EFSA Scientific Report (2005) 30, pp. 1-46.
"1-Methylcyclopropene; Amendment to an Exemption from the Requirement of a Tolerance," Federal Register, vol. 73, No. 69 (Apr. 9, 2008) Rules and Regulations pp. 19147-19150.
"Ethylbloc Registration No. 71297-1 and Ethylbloc Sachet Registration No. 71297-5," Firm No. 71297, Agro Fresh Inc. Philadelphia, PA. http://ppis.ceris.purdue.edu/htbin/rnamset.com (Feb. 2, 2011) 3 pgs.
Trademark Search for "ETHYLBLOC" http://tess2.uspto.gov/bin/showfield?f+doc&state+4005:6v38ie.2.1 (Feb. 11, 2011) 2 pgs.
"ExxonMobilTM LDPE LGA 105, Low Density Polyethylene Resin," ExxonMobil Chemical, www.exxonmobilpe.com (Nov. 6, 2009) 2 pgs.
"ExxonMobilTM PP3155: Polypropylene Homopolymer ExxonMobil Chemical," IDES Prospector, IDES—The Plastics Web, www.ides.com (Nov. 6, 2009) 1 pg.
"FAO Specifications and Evaluations for Agricultural Pesticides 1-Methylcyclopropene," 2008, 30 pgs.
Fatty Acid Melting Points <http://www.chemicalland21.com/lifescience/foco/BEHENIC%ACID.htm> Nov. 21, 2013.
"FusabondR P MD411D," IDES Prospector, www.ides.com (Nov. 6, 2009) 1 pg.
Hotchkiss, J.H. et al. "Release of 1-Methylcyclopropene from Heat-Pressed Polymer Films," Journal of Food Science, vol. 72, No. 5, 2007. Section E: Food Engineering & Physical Properties, E330-E334.
Husken, Debby "Hydrophilic Segmented Block Copolymers Based on Poly(Ethylene Oxide)" 2006, 199 pgs.
Hwang, Suzie J. et al. "Effects of Structure of B-Cyclodextrin-Containing Polymers on Gene Delivery," Bioconjugate Chem. 12 (2001) pp. 280-290.
"IntegrateTM NE542013, Functionalized Polyolefin, Melt Index 13, Density 0.943," Equistar, Lyondell Chemical Company, Houston, Texas, http://www.Lyondell.com (Mar. 2006) 1 pg.
Jiang, Yueming et al. "Extension of the shelf life of banana fruit by 1-methylcyclopropene in combination with polyethylene bags," Postharvest Biology and Technology 16 91999) pp. 187-193.
Lee, Younsuk S. et al. "Development of a 1-Methylcyclopropene (1-MCP) Sachet Release System," Journal of Food Science, vol. 71, No. 1, (2006) Section C: Food Chemistry & Toxicology, pp. C1-C6.
"AlathonM6210High Density Polyethylene; MMW Film Grade, Melt Index 0.95, Density 0.958." Data Sheet, Lyondell Chemical Company, Houston Texas.
Macnish, Andrew J. et al. "A simple sustained release device for the ethylene binding inhibitor 1-methylcyclopropene," Institute of BioScience and Technology, Cranfield University at Silsoe, Befordshire MK45 4DT, UK. 50 pgs.
Nanthachai, Nunchanok et al. "Absorption of 1-MCP by fresh produce," Postharvest Biology and Technology, 43 (2007) pp. 291-297.
Neoh, Tze Loon et al. "Kinetics of Molecular Encapsulation of 1-Methylcyclopropene into a-Cyclodextrin," Journal of Agriculture and Food Chemistry, 55 (2007) pp. 11020-11026.
Neoh, Tze Loon et al. "Kinetic Study of Thermally Stimulated Dissociation of Inclusion Complex of 1-Methylcyclopropene with a-Cyclodextrin by Thermal Analysis," J. Phys. Chem. B, vol. 112, No. 49 (2008) pp. 15914-15920.
Parafilm® M, Brand, "Seals tightly, quickly and universally: Parafilm® M Sealing Film." GmbH + Co., Wertheim, Germany, 4 pages.
Schotsmans et al. "Methylcyclopropene: Mode of action and relevance in postharvest horticulture research", Horticultural Reviews, vol. 35, Purdue University. 2009. Chapter 5, pp. 263-313.
Blankenship, Sylvia. "Ethylene: The Ripening Hormone", Postharvest Information Network, WSU Tree Fruit Research & Extension Center, obtained Nov. 28, 2012 from <http://postharvest.tfrec.wsu.edu/pages/PC2000F>, 2 pages.
Office Action dated May 18, 2015 in connection with Taiwanese Patent Application No. 101110340, with English Translation.

(56) References Cited

OTHER PUBLICATIONS

Final Official Action dated May 20, 2015 in connection with Japanese Patent Application No. 2012-544678, with English Translation.
First Examination Report dated May 12, 2015 in connection with Australian Patent Application No. 2014203711.
English Translation of Official Communication dated Jul. 7, 2015 in connection with Israeli Patent Application No. 228558.
Non-Final Office Action dated Apr. 9, 2015 in U.S. Appl. No. 14/619,905, 9 pages.
Office Action dated Mar. 5, 2015 in Russian Patent Application No. 2012129253 and English Translation, 8 pages.
Office Action dated Mar. 19, 2015 in European Patent Application No. 10795543.7, 3 pages.
Examination Report dated Apr. 1, 2015 in Canadian Patent Application No. 2831213, 3 pages.
First Office Action dated Aug. 3, 2015 in Chinese Patent Application No. 201410461847X.
Notification of Defects dated Aug. 31, 2015 in Israeli Patent Application No. 228558.
Office Action dated Oct. 20, 2015 in Ukrainian Patent Application No. a 2013 12523, including English translation.
First Examination Report dated Sep. 2, 2015 in Australian Patent Application No. 2014227556.
Notification of Defects dated Sep. 17, 2015 in Israeli Patent Application No. 238943.
Supplemental European Search Report dated Oct. 12, 2015 in European Patent Application No. 13828965.7.
Official Notice of Preliminary Rejection dated Oct. 28, 2015 in connection with Korean Patent Application No. 10-2015-7017463.
Communication pursuant to Article 94(3) EPC dated Oct. 29, 2015 in connection with European Patent Application No. 13828965.7.
Extended European Search Report dated Dec. 18, 2015 in connection with European Patent Application No. 15180902.7.
Official Action dated Dec. 9, 2015 in connection with Chilean Application No. 2013-02795.
Communication pursuant to Article 94(3) dated Mar. 4, 2016 in connection with European Patent Application No. 10795543.7.
Office Action dated Jan. 26, 2016 in connection with Japanese Patent Application No. 2015-545208.

* cited by examiner

CONTROLLED RELEASE COMPOSITIONS AND METHODS OF USING

BACKGROUND

There is a substantial need in the art for improved plant maturation and degradation prevention. In particular, pressure from worldwide urbanization, manufacturing, and population growth necessitates development of new technologies to increase the efficiency and yield of natural resources expended on delivering food to the growing global population. In the United States, for example, it is estimated that between 8% and 16% of profit loss of fresh produce is due to spoilage and shrinkage which is estimated at $8-$28 Billion system wide. This loss translates to significant wasted resources, for example pesticides, fertilizer, and herbicide use; land and water use; transportation, including oil and gas use; and resources associated with the storage of produce. Loss of these and other resources are due to inefficiencies in production and delivery that allows significant spoilage of fruits and vegetables before these critical products can reach the consumer. The United Nations Asian and Pacific Centre for Agricultural Engineering and Machinery's Feasibility Study on the Application of Green Technology for Sustainable Agriculture Development states:

"Technology is a link that connects sustainability with enhanced productivity, where natural resource productivity is efficiently maintained by carefully planning the conservation and exploitation of resources such as soil, water, plants, and animals."

(Feasibility Study on the Application of Green Technology for Sustainable Agriculture Development, United Nations Asian and Centre for Agricultural Engineering and Machinery, http://www.unapcaem.org/publication/GreenTech.pdf, at p. 20.) Climate change is raising the stakes for agricultural technology as the world population grows and the amount of arable land shrinks. More mouths to feed, plus less arable land and changing rainfall patterns, means growing demand for technology that lets farmers do more with less. The European Commission recently announced an initiative to optimize food packaging without compromising safety in order to reduce food waste (Harrington, R., "Packaging placed centre stage in European food waste strategy," http://www-.foodqualitynews.com/Public-Concerns/Packaging-placed-centre-stage-in-European-food-waste-strategy). The initiative is in response to recent findings that up to 179 kg of food per person is wasted each year. The plan stresses the need for innovation, such as "active packaging" or "intelligent packaging" as one aspect of the solution. Technology that addresses the issue of fruit and vegetable spoilage is therefore of critical importance as a "green" technology that reduces waste of food and its associated resources by increasing the effective efficiency of arable land.

The shelf life of produce or produce materials, including whole plants and parts thereof including fruits, vegetables, tubers, bulbs, cut flowers and other active respiring plants or plant materials, is typically determined, at least in part, by the amount of an ethylene generated by the respiring plant material. Ethylene is a known plant ripening or maturation hormone. At any appreciable concentration of ethylene in and around living plant material, the maturation of the plant is initiated, maintained or accelerated, depending on concentration. Ethylene-sensitive and -insensitive horticultural commodities (produce and ornamentals) are categorized as being climacteric or non-climacteric on the basis of the pattern of ethylene production and responsiveness to externally added ethylene. Climacteric crops respond to ethylene by an early induction of an increase in respiration and accelerated ripening in a concentration-dependent manner. Non-climacteric crops ripen without ethylene and respiration bursts. However, some non-climacteric crops are sensitive to exogenous ethylene, which can significantly reduce postharvest shelf life. Non-climacteric produce harbor several ethylene receptors which are active. Therefore, exposure of non-climacteric produce to exogenous ethylene can trigger physiological disorders shortening shelf life and quality. See, Burg et al., *Plant Physiol.* (1967) 42 144-152 and generally Fritz et al. U.S. Pat. No. 3,879,188. Many attempts have been made to either remove ethylene from the ambient package atmosphere surrounding the produce or to remove ethylene from the storage environment in an attempt to increase shelf life. Reduced ethylene concentration is understood to be achieved through a decrease in the stimulus of a specific ethylene receptor in plants. Many compounds other than ethylene interact with this receptor: some mimic the action of ethylene; others prevent ethylene from binding and thereby counteract its action.

Many compounds that act as an antagonist or inhibitor block the action of ethylene by binding to the ethylene binding site. These compounds may be used to counteract ethylene action. Unfortunately, they often diffuse from the binding site over a period of several hours leading to a longer term reduction in inhibition. See E. Sisler and C. Wood, *Plant Growth Reg.* 7, 181-191 (1988). Therefore, a problem with such compounds is that exposure must be continuous if the effect is to last for more than a few hours. Cyclopentadiene has been shown to be an effective blocking agent for ethylene binding. See E. Sisler et al., Plant Growth Reg. 9, 157-164 (1990). Methods of combating the ethylene response in plants with diazocyclopentadiene and derivatives thereof are disclosed in U.S. Pat. No. 5,100,462 to Sisler et al. U.S. Pat. No. 5,518,988 to Sisler et al. describes the use of cyclopropenes having a $C_{1-4}$ alkyl group to block the action of ethylene.

Another suitable olefinic antagonist or inhibitor of receptor sites or ethylene generation in produce is 1-methylcyclopropene (1-MCP). Derivatives and analogs thereof are also known to have antagonizing or inhibiting effects for the generation of ethylene from respiring plant or produce material or the reception thereof by receptors present on the living plant material. Olefins including 1-MCP, 1-butene and others have been shown to have at least some measurable activity for extending shelf life via such a mechanism. A number of proposals have been made for the method of producing and releasing 1-MCP to slow maturation and maintaining the quality of plant materials. Currently 1-MCP is dispensed by the release of 1-MCP from a moisture activated powder or sachet containing complexed 1-MCP. In these technologies, 1-MCP is released from a point source which causes a concentration gradient within the storage chamber thus resulting in a variation in maturation inhibition wherein some produce has an extended life time where other produce exposed to a lesser concentration 1-MCP tends to have less inhibition of ethylene and has a reduced shelf life.

Further, 1-MCP is a gas in its natural state and is prone to violent autopolymerization (see e.g. EFSA Scientific Report (2005) 30, 1-46, Conclusion on the peer review of 1-methylcyclopropene, 2 May 2005). For this reason, 1-MCP is typically complexed with carrier materials such as α-cyclodextrin (see, e.g., Toivonen et al., U.S. Patent Publication No. 2006/0154822). However, even when this is done, there are problems that still persist. The 1-MCP will rapidly release when exposed to water and/or water vapor. (Neoh, T. L., et al., *Carbohydrate Research* 345 (2010) 2085-2089). This is the intended result, once the 1-MCP is located, for example, inside the headspace of a package containing live plant material. However, if the cyclodextrin/1-MCP complex is not protected from exposure to liquid water and/or water vapor prior to the intended use—that is, during processing and storage—the 1-MCP will be prematurely released, and thus much if not all of the effectiveness of the complex will be lost prior to arrival at the intended use site.

Additionally, the cyclodextrin/1-MCP complex is heat sensitive, wherein loss of 1-MCP is initiated even in dry environments when the temperature reaches about 90° C. (Neoh, T. L., et al., *J. Phys. Chem. B* 2008, 112, 15914-15920). Further, in such cases, exposure of released 1-MCP gas to elevated temperatures can lead to an increased risk of autopolymerization. Thus, there is a need for an improved system of delivering plant spoilage retarding materials such as 1-MCP into the headspaces of plant storage units such that there is not a premature release of the active before it is ready to be used.

While not suffering from the hazards of autopolymerization, other compounds desirably incorporated into cyclodextrin inclusion complexes for later release in an end use application, such as fragrances or antimicrobial compounds, suffer from premature loss of the complexed compounds during processing at elevated temperatures, in the presence of ambient humidity, or both. Additionally, some fragrance or antimicrobial compounds are not considered useful in conjunction with the cyclodextrin complex delivery systems described in the art, because of the high temperatures employed in processing. In such cases, it is specifically noted that e.g. fragrance molecules having low boiling points must be avoided, since they will be gone by the time the high-temperature polymer extrusion processing required to deliver the complex is completed. See, e.g. U.S. Pat. No. 7,019,073. Such cyclodextrin inclusion complex delivery systems would also benefit from the availability of a delivery vehicle that provides for an improved yield of the inclusion complex for availability at the targeted application.

BRIEF SUMMARY OF THE INVENTION

Disclosed herein is a composition that includes, or is substantially, a cyclodextrin inclusion complex and a carrier, wherein the cyclodextrin complex includes a cyclodextrin compound and an olefinic inhibitor, and the carrier has a melting transition onset between about 23° C. and 40° C. and solubility in water of less than 1 wt % at 25° C. In some embodiments, the cyclodextrin inclusion complex consists of α-cyclodextrin and 1-methylcyclopropene. In some embodiments, the carrier has a kinematic viscosity of less than about 30 cP at 100° C. In some embodiments, the carrier includes, or is substantially only petrolatum or a non-petroleum sourced material having properties similar to petrolatum.

Also disclosed herein is a treated substrate. The treated substrate includes the composition as described above disposed on a substrate. In some such embodiments, the composition is present in a discontinuous pattern on the substrate. In some embodiments, the treated substrate is a treated laminate. In some embodiments, a container includes the treated substrate. In various embodiments, the container is enclosed, partially enclosed, or unenclosed. In some embodiments, the container includes one or more items of produce. In some embodiments, the atmosphere proximal to the produce comprises between 1 ppb and 5 ppm of the olefinic inhibitor.

Also disclosed herein is a method of making a treated substrate. The method includes heating the composition described above to a temperature between 60° C. and 80° C., and disposing the heated composition on a first substrate using a flexographic printing press. In some embodiments, the method further includes cooling the treated substrate, wherein the cooling is accomplished using a chill roll on the flexographic printing press. In some embodiments, the printing is accomplished using a discontinuous printed pattern. In some such embodiments, the treated substrate has 50% or less of the available substrate surface area having the composition printed thereon in a discontinuous printed pattern. In some embodiments, the composition is contacted with a second substrate after the printing, and optionally after the cooling. In some such embodiments, an adhesive is disposed between the second substrate and the composition.

Also disclosed herein is a method of printing a printable media composition on a substrate. The printable media composition includes, or is substantially, a cyclodextrin inclusion complex and a printable media, wherein the cyclodextrin complex includes a cyclodextrin compound and a complexed compound, and the printable media has a kinematic viscosity of less than about 30 cP at 100° C. The printing is carried out by heating the printable media composition to a temperature between 50° C. and 100° C., and printing the heated printable media composition on a first substrate using a flexographic printing press. In some embodiments, the complexed compound is an olefinic inhibitor. In embodiments, the printing is pattern printing, wherein the pattern is a discontinuous pattern. In some such embodiments, less than 50% of the available surface area of the substrate is printed with the discontinuous pattern.

Also disclosed herein is the printed substrate obtained by the printing method described above. The printed substrate includes the printable media composition as described above, flexographically printed on a substrate. In some embodiments, the printable media composition is flexographically printed in a discontinuous pattern. In some embodiments, the printed substrate is a printed laminate, wherein a second substrate is disposed over the printable media composition after the flexographic printing. In some such embodiments, an adhesive is disposed between the printable media composition and the second substrate. In some embodiments, a printed container includes the printed substrate. In some such embodiments, the printed container is enclosed, partially enclosed, or unenclosed. In some embodiments, the printed container includes one or more items of produce. In some embodiments, the complexed compound is an olefinic inhibitor and the atmosphere proximal to the produce comprises between 1 ppb and 5 ppm of the olefinic inhibitor.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

DETAILED DESCRIPTION OF THE INVENTION

Figure 1:
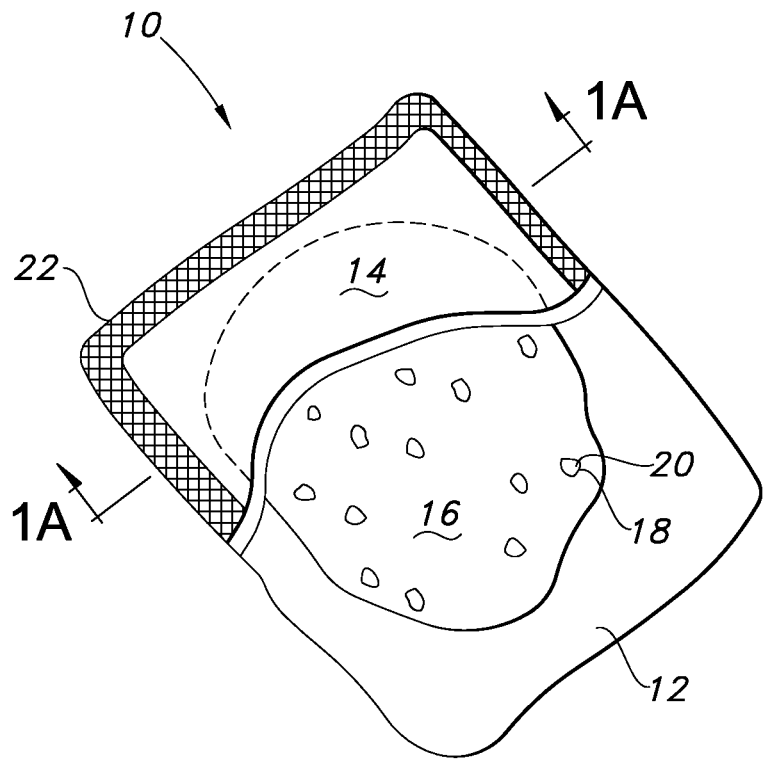
FIG. 1 is a cutaway perspective view of an article according to the present invention.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

1. Definitions

As used herein, the term "cyclodextrin" or "cyclodextrin compound" means a cyclomalto-oligosaccharide having at least five glucopyranose units joined by an α(1-4) linkage. Examples of useful cyclodextrins include α-, β-, or γ-cyclodextrin wherein α-cyclodextrin has six glucose residues; β-cyclodextrin has seven glucose residues, and γ-cyclodextrin has eight glucose residues. Cyclodextrin molecules are characterized by a rigid, truncated conical molecular structure having a hollow interior, or pore, of specific volume. "Cyclodextrin" can also include cyclodextrin derivatives as defined below, or a blend of one or more cyclodextrins compounds. The following table recites properties of α-, β-, and γ-cyclodextrin.

| CYCLODEXTRIN TYPICAL PROPERTIES | | | |
| --- | --- | --- | --- |
| CD PROPERTIES | α-CD | β-CD | γ-CD |
| Degree of polymerization (n =) | 6 | 7 | 8 |
| Molecular Size (A°) | | | |
| inside diameter | 5.7 | 7.8 | 9.5 |
| outside diameter | 13.7 | 15.3 | 16.9 |
| height | 7.0 | 7.0 | 7.0 |
| Specific Rotation $[\alpha]^{25}_D$ | +150.5 | +162.5 | +177.4 |
| Color of iodine complex | Blue | Yellow | Yellowish Brown |
| Solubility in Distilled water (g/100 mL) 25° C. | 14.50 | 1.85 | 23.20 |

As used herein, the term "cyclodextrin derivative" or "functionalized cyclodextrin" means a cyclodextrin having a functional group bonded to one of the cyclodextrin glucose moiety hydroxyl groups. Nonlimiting examples of cyclodextrin derivatives are described in U.S. Pat. No. 6,709,746.

As used herein, the term "cyclodextrin inclusion complex" means the combination of a complexed chemical compound, or "complexed compound", and a cyclodextrin wherein a complexed compound is disposed within the pore of the cyclodextrin ring. The complexed compound must satisfy the size criterion of fitting at least partially into the cyclodextrin internal cavity or pore, to form an inclusion complex. The cyclodextrin inclusion complexes include, inherent to the formation and existence of the inclusion complex, some amount of "uncomplexed" cyclodextrin; this is because (1) in embodiments synthesis of the inclusion complex does not result in 100% formation of inclusion complex; and (2) in embodiments, the inclusion complex is in equilibrium with the corresponding uncomplexed cyclodextrin/uncomplexed compound. Each cyclodextrin/compound combination has a characteristic equilibrium associated with its inclusion complex under a given set of conditions, including temperature, pressure, and humidity conditions. In some embodiments, the complexed compound is an olefinic inhibitor compound.

As used herein, the term "olefinic inhibitor", "olefinic inhibitor compound" or "olefinic inhibitor of ethylene generation" is intended to mean an olefinic compound that contains at least one olefinic double bond, has from about 3 to about 20 carbon atoms and can be aliphatic or cyclic having at least minimal ethylene antagonist or inhibition activity.

As used herein, the term "cyclodextrin composition" means a composition including, consisting essentially of, or consisting of a cyclodextrin inclusion complex and a hydrophobic carrier. As used herein, the term "hydrophobic carrier" or "carrier" means a compound or miscible blend of compounds that meets the following criteria:

1. Melting transition onset of between about 23° C. and 40° C.; and
2. At least one of the following:
   a. water contact angle to the carrier surface of 90° or greater, measured according to ASTM D7334-08 (ASTM International, W. Conshohocken, Pa.); or
   b. solubility in water of less than 1 wt % at 25° C.

"Melting transition onset" means a change in the heat capacity corresponding to the onset of melting, $T_m$, the completion of which corresponds to the complete melting of a material as indicated by the peak heat capacity. From the integral of this peak, the enthalpy of melting can be determined; and from the onset the melting temperature is determined. All measurements of heat capacity as a function of temperature are measured by differential scanning calorimetry (DSC). As used herein, "melt transition onset" means the melt transition onset measured by DSC over the range −20° C. to 150° C., heating at 10° C./min. In some embodiments, the carrier has a kinematic viscosity of less than 30 mm²/s at a temperature of 100° C. In some embodiments, the carrier includes at least one compound or blend of compounds that has a chemical structure that is at least 50 mole % hydrocarbon or dimethylsiloxane. "Hydrocarbon" means consisting of carbon and hydrogen. "Dimethylsiloxane" means a repeating unit consisting of —Si(CH$_3$)$_2$—O—. In embodiments, the carrier is characterized by the substantial absence of hydrophilic compounds, wherein "substantial" means, in this context, that the presence of hydrophilic compounds is not sufficient to reduce the water contact angle to below 90°.

As used herein, the term "substrate" means a solid article having at least one surface capable of receiving a cyclodextrin composition. Substrates are not particularly limited as to makeup, shape, or regarding parameters such as size or thickness. In embodiments, a substrate includes at least one surface that is suitable for coating or printing a cyclodextrin composition thereon. Representative examples of substrates include items of produce, thermoplastic or thermoset webs, sheets, and films; metal articles, sheets or foils; glass articles, sheets, or plates; coated or uncoated paper or cardboard articles, webs or sheets; combined or multilayer web, sheet, or film constructions formed from a combination of two or more thermoplastics, thermosets, paper, cardboard, glass, or metals; wrappings, bags, boxes, cartons, punnets, or other articles; articles formed from webs, sheets, films, glass, metals, metal foils, or combinations thereof; wax or film coatings; paper or thermoplastic labels, adhesives used to close or seal packaging or adhere labels and the like thereto; perforated, porous, or permeable films; open-celled or closed-cell foams; netting or mesh formed from cellulosic or thermoplastic materials; fibers, including cellulosic and synthetic fiber materials, staple fibers, microfibers, and nanofibers, and woven, felted, or nonwoven fabrics formed from the fibers; and the like.

As used herein, the term "container" means a self-contained unit for holding produce, or a component of such a self-contained unit. In some embodiments, a container is also a substrate when employed to receive a cyclodextrin composition disposed thereon. In various embodiments, containers are formed from flexible, semi-rigid, or rigid materials, or combinations thereof. Containers are not particularly limited as to content of the material from which they are made, or by parameters such as overall size, thickness of unit walls or floors, etc. Non-limiting examples of containers include punnets, dishes, cups, lids, covers, wrapping film, packing foam, sealing tapes, labels, ties, closures, caps, bags, boxes, pouches, envelopes, cartons, netting sacks, refrigerated trucks, shipping containers, warehouse or storage rooms, buildings or sections thereof, and the like. In various embodiments, a container defines an enclosed space, such as a sealed bag or a closed-cell foam; a partially enclosed space, such as a punnet, open-celled foam, or a permeable or perforated bag; or no enclosed space, such as an open carton or a netting bag.

As used herein, the term "treated substrate" means a substrate having a cyclodextrin composition disposed on at least a portion of a surface thereof.

As used herein, the term "treated laminate" means an article including a first substrate having a cyclodextrin composition disposed on at least a portion of a surface thereof, and a second substrate disposed over the cyclodextrin composition, wherein the first and second substrates are the same or different. In some embodiments, the second substrate is not solid upon contacting the cyclodextrin composition but is solidified after contacting the cyclodextrin composition, such as by cooling or chemical reaction. In general and as determined by context below, discussion of treated substrates include treated laminates. In some embodiments, one of the first or second substrates is removable; in some such embodiments, the removable substrate is referred to as a "liner."

As used herein, the term "treated container" means a container that includes a cyclodextrin composition. In embodiments the treated container includes a treated substrate or a treated laminate. In some embodiments, the treated container is formed from a treated substrate or a treated laminate. In some embodiments the treated container includes a treated substrate as an integral part of the container. In some embodiments, a container is a substrate, and the cyclodextrin composition is disposed thereon to form the treated container. In some embodiments, a treated substrate or a treated laminate is added to a container to form the treated container.

As used herein, the term "article" means a substrate, a container, a treated substrate, a treated container, a treated laminate, or a combination of two or more thereof.

The term "produce" or "produce material" includes any whole plant, plant part, such as a fruit, flower, cut flower, seed, bulb, cutting, root, leaf, flower, or other material that is actively respiring and, as a part of its maturation, generates ethylene as a maturation hormone (climacteric) or ripens without ethylene and respiration bursts (non-climacteric).

As used herein, the term "permeable" as applied to a cyclodextrin composition or an article, means that the composition or article has a permeability to the complexed compound of equal to or greater than 0.01 ($cm^3 \cdot mm/m^2 \cdot 24$ hrs·bar) at standard temperature and pressure (STP) and 0% relative humidity; or permeability to water vapor of equal to or greater than 0.1 ($g \cdot mm/m^2 \cdot 24$ hr) at 38° C. and 90% relative humidity, when measured according to ASTM D96; or permeability to $O_2$ of equal to or greater than 0.1 ($cm^3 \cdot mm/m^2 \cdot 24$ hr·bar) at 23° C. and 0% relative humidity, when measured according to ASTM D3985; or permeability to $CO_2$ of equal to or greater than 0.1 ($cm^3 \cdot mm/m^2 \cdot 24$ hr·bar) at 23° C. and 0% relative humidity, when measured according to ASTM D1434; or a combination of two or more thereof.

As used herein, the term "impermeable" as applied to a cyclodextrin composition or an article means that the cyclodextrin composition or article has a permeability to the complexed compound of less than 0.01 ($cm^3 \cdot mm/m^2 \cdot 24$ hrs·bar) at STP and 0% relative humidity; or permeability to water vapor of less than 0.1 ($g \cdot mm/m^2 \cdot 24$ hr) at 38° C. and 90% relative humidity, when measured according to ASTM D96; or permeability to $O_2$ of less than 0.1 ($cm^3 \cdot mm/m^2 \cdot 24$ hr·bar) at 23° C. and 0% relative humidity, when measured according to ASTM D3985; or permeability to $CO_2$ of less than 0.1 ($cm^3 \cdot mm/m^2 \cdot 24$ hr·bar) at 23° C. and 0% relative humidity, when measured according to ASTM D1434; or a combination of two or more thereof.

As used herein, the term "discontinuous" means having intervals or gaps. As applied to printing operations, discontinuous means a regular or irregular printing pattern having intervals or gaps unprinted by a cyclodextrin composition or a printable media composition. In some embodiments other materials—including other printed materials—are present in such intervals or gaps, for example; but the other materials do not include a cyclodextrin composition or printable media composition.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

As used herein, the term "substantially" means "consisting essentially of", and includes "consisting of", generally and unless otherwise specified, as those terms are construed within patent claim language in the United States as of the date of the filing of this application. For example, a solution that is "substantially free" of a specified compound or material may be free of that compound or material, or may have a trace amount of that compound or material present, such as through aging, unintended contamination, or incomplete purification. A composition that has "substantially only" a provided list of components may consist of only those components, or have trace amounts of one or more additional components present, or have one or more additional components present that do not materially affect the properties of the composition. And a "substantially planar" surface may have minor defects, or embossed features that do not materially affect the overall planarity of the film.

2. Cyclodextrin Compositions and Treated Substrates

We have found that one or more cyclodextrin inclusion complexes are useful to form a cyclodextrin composition using mild conditions. In embodiments, the cyclodextrin compositions are disposed on at least a portion of a surface of a substrate to form a treated substrate. In other embodiments, the cyclodextrin compositions are disposed on at least a portion of a surface of a first substrate and a second substrate is disposed over the cyclodextrin composition to form a treated laminate. In embodiments, a treated substrate or a treated laminate is either included in, or is used to form a treated container.

The cyclodextrin compositions of the invention include at least a cyclodextrin inclusion complex and a carrier. The cyclodextrin employed to form the cyclodextrin inclusion complex is selected for the specific volume of the cyclodextrin pore. That is, the cyclodextrin pore size is selected to fit the molecule size of the compound used to complex with the cyclodextrin. In embodiments, the complexed compound is an olefinic inhibitor. The olefinic inhibitor is a compound having from 3 to about 20 carbon atoms, comprising at least one olefinic bond and a cyclic, olefinic or diazo-diene structure. In some embodiments, the olefinic inhibitor has the following structure:

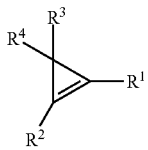

wherein each of $R^1$, $R^2$ are independently hydrogen or a $C_{1-16}$ hydrocarbyl group and $R^3$ and $R^4$ are independently hydrogen or a $C_{1-16}$ hydrocarbyl group with the proviso that at least one of $R^1$ or $R^2$ is methyl.

Representative examples of compounds useful as the olefinic inhibitor of ethylene generation include 1-methyl cyclopropene, 1-butene, 2-butene, and isobutylene. Of these, 1-methyl cyclopropene, or "1-MCP", has been found to be particularly useful. It has been found that 1-MCP has a molecular size that is suitable for formation of an inclusion complex when combined with α-cyclodextrin, or α-CD.

In embodiments, the inclusion complex of α-CD with 1-MCP, or "1-MCP/c/α-CD", contains about 0.10 to 0.99 mole of the olefinic inhibitor per mole of cyclodextrin, or about 0.20 to 0.95 mole of the olefinic inhibitor per mole of cyclodextrin, or about 0.30 to 0.90 mole of the olefinic inhibitor per mole of cyclodextrin, or about 0.50 to 0.90 mole of the olefinic inhibitor per mole of cyclodextrin, or about 0.50 to 0.80 mole of the olefinic inhibitor per mole of cyclodextrin, or about 0.30 to 0.70 mole of the olefinic inhibitor per mole of cyclodextrin, or any combination of the above listed value ranges, for example, about 0.70 to 0.80 mole of the olefinic inhibitor per mole of cyclodextrin, 0.90 to 0.95 mole of the olefinic inhibitor per mole of cyclodextrin, 0.10 to 0.20 mole of the olefinic inhibitor per mole of cyclodextrin, and the like.

In other embodiments, the complexed compound is an antimicrobial compound. Examples of antimicrobial compounds usefully complexed with cyclodextrin, most commonly but not exclusively β-cyclodextrin, include chlorine dioxide, ethanol, triclosan (5-chloro-2-(2,4-dichlorophenoxy)phenol), amyl phenol, phenyl phenol, catechin, p-cresol, hydroquinones, benzyl-4-chlorophenol, short chain alkyl parabens, short chain alkyl esters of p-hydroxybenzoic acid, 3,4,4'-trichlorocarbanilide, benzoic anhydride, sorbic anhydride, octanal, nonal, cis-2-hexenal and trans-2-hexenal, 2,2-diphenyl-1-picrylhydrzyl, organic acids such as acetic acid, propanoic acid, benzoic acid, citric acid, lactic acid, malic acid, propionic acid, sorbic acid, succinic acid, and tartaric acid as well as salts thereof, such as calcium sorbate, potassium sorbate, and sodium benzoate; hexamethylenetetramine, silicon quaternary ammonium salts, phosphoric acid, chitosan and chitooligosaccharides, Konjac glucomannan, Natamycin, Reuterin, peptides such as Attacin, Cecropin, Defensin, and Magainin; antioxidants such as butylated hydroxyanisole (BHA), phenolic butylated hydroxytoluene (BHT), and t-butylhydroquinone (TBHQ); bacteriocins such as Bavaricin, Brevicin, Carnocin, Imazalil, Lacticin, Mesenterocin, Nisin, Pediocin, Propolis, Sakacin, and Subtilin; chelators such as citrates, conalbumin, EDTA, lactoferrin, and polyphosphates; essential oils such as cinnamon bark oil, citron oil, coriander oil, eucalyptus oil, lavender oil, lemon grass oil, peppermint oil, perilla oil, rosemary oil, tea oil, Ajwain oil, basil oil, caraway oil, citronella oil, coriander oil, clove oil, Fenugreek oil, ginger oil, mustard oil, oregano (oreganum) oil, paprika oil, and thyme oil; fatty acids and esters thereof, wherein fatty acids include lauric acid, palmitoleic acid, and monolaurin and fatty acid monoesters include glycerol monolaurate, glycerol monocaprate, propylene glycol monolaurate, and propylene glycol monocaprate; fungicides such as Benomyl, Imazalil, and sulfur dioxide; methyl-(glucocapparin), ethyl-(glucolepidiin), propyl-(glucoputranjivin), n-butyl-(glucocochlearin), allyl-(sinigrin), metals such as copper and silver; allyl isothiocyanate (AIT), camphor, carvacrol, cineole, cinnamaldehyde, citral, p-cymene, estragole (methyl chavicol), eugenol, geraniol, geranyl acetate, hinokitiol (β-thujaplicin), limonene, linalool, p-menthone, menthol, neral, perillaldehyde, α-pinene, γ-terpinene, terpineol, thymol, mixtures of two or more thereof, and the like.

In other embodiments, the complexed compound is a fragrance compound. Usefully complexed fragrance compounds include compounds such as amyl cyanamid, benzyl salicylate, amyl cinnamic aldehyde, citral, benzophenone, cedrol, cedryl acetate, dihydroisojasmonate, diphenyl oxide, patchouli alcohol, musk ketone, and the like, but lower-boiling compounds such as certain low-boiling essential oils and lower esters are also useful in embodiments.

In still other embodiments, the compositions of the invention include a mixture of complexed compounds that include one or more fragrance compounds and one or more antimicrobial compounds. In still other embodiments, the compositions of the invention include a mixture of complexed compound that include an olefinic inhibitor and an antimicrobial compound. Due to the ease of forming the cyclodextrin complexes, the ease of forming the compositions, and the ease of using the compositions by disposing them on one or more substrates, such blended and multiple use compositions are easily envisioned and employed by one of skill in any ratio suitable for a targeted application.

Methods employed to form cyclodextrin inclusion complexes are known and are found in the literature. Typical methods involve admixing the cyclodextrin and the compound to be complexed in aqueous solution for a period of time sufficient to form the inclusion complex. However, the use of 1-MCP or other low-boiling olefinic inhibitors as the complexed compound involves adjustment of the methodology to account for the need to complex cyclodextrin with a gas at common ambient temperatures (1-MCP has a boiling point of 12° C.). The inclusion complex of α-cyclodextrin and 1-MCP, also referred to herein as "1-MCP/c/α-CD", is known, and method of forming it are described, for example, in U.S. Pat. Nos. 6,017,849 and 6,548,448 as well as in Neoh, et al., *J. Agric. Food Chem.* 2007, 55, 11020-11026. In one method, α-cyclodextrin is dissolved in water and 1-MCP is bubbled into the solution for a period of time at room temperature. The inclusion complex precipitates from the solution as it forms and thus is easily isolated by simple filtration followed by vacuum drying. The dried cyclodextrin inclusion complex is then ready for use. Storage in a dry container with minimal head space is sufficient.

In some embodiments, a cyclodextrin inclusion complex is formed with a cyclodextrin derivative. Cyclodextrin derivatives are employed to form the inclusion complex in some embodiments to improve miscibility in the cyclodextrin composition. Cyclodextrin derivatives employed to improve miscibility of the cyclodextrin composition include any of the cyclodextrin derivatives described in U.S. Pat. No. 6,709,746 or in Croft, A. P. and Bartsch, R. A., *Tetrahedron Vol.* 39, No. 9, pp. 1417-1474 (1983). In some embodiments where a cyclodextrin derivative is employed to form the cyclodextrin inclusion complex, the olefinic inhibitor is introduced in a non-water solvent, for example a hydrocarbon having 1 to 10 carbons, an alcohol having 1 to 10 carbons, a heterocyclic or aromatic solvent having 4 to 10 carbons. In some such embodiments, blends of one or more solvents are employed. In other embodiments, the inclusion complex is formed prior to functionalization of the cyclodextrin derivative. In such embodiments, care must be taken during the functionalization to employ techniques and select functional group chemistries that avoid displacing the olefinic inhibitor from the inclusion complex, for example by preferential inclusion of one of the compounds employed in the functionalization. The cyclodextrin composition is an admixture of the cyclodextrin inclusion complex and a hydrophobic carrier. The carrier is defined by a low melting point and high hydrophobicity. The carrier is a compound or miscible blend of compounds that meets the following criteria:
1. Melting transition onset of between about 23° C. and 40° C., as measured by DSC at 10° C./min between –20° C. and 150° C.; and
2. One or more of the following:
    a. water contact angle to the carrier surface of 90° or greater, measured according to ASTM D7334-08 (ASTM International, W. Conshohocken, Pa.);
    b. solubility in water of less than 1 wt % at 25° C.

The melting transition onset of the carrier is between about 23° C. and 40° C. when measured by DSC by subjecting the carrier to a temperature range of –20° C. to 150° C., heating at 10° C. per minute; in some embodiments the melting transition onset is between about 23° C. and 38° C., or between about 23° C. and 36° C., or between about 23° C. and 34° C., or between about 25° C. and 38° C., or between about 25° C. and 36° C., or between about 25° C. and 35° C. In some embodiments, the water contact angle of the carrier surface is between about 80° and 160°, or between about 90° and 120°. The carrier has solubility in water of less than 1 wt % at 25° C., for example about 0.0001 wt % to 0.99 wt % at 25° C., or about 0.001 wt % to 0.90 wt % at 25° C., or about 0.01 wt % to 0.75 wt % at 25° C., or about 0.01 wt % to 0.50 wt % at 25° C., or about 0.01 wt % to 0.10 wt % at 25° C., or about 0.0001 wt % to 0.10 wt % at 25° C.

In some embodiments, the carrier has a kinematic viscosity of less than 30 mm$^2$/s at a temperature of 100° C., for example a dynamic viscosity of between 1 cP and 30 cP at 100° C., or between 1 cP and 30 cP at 90° C.

In some embodiments, the carrier includes at least one compound or blend of compounds that has a chemical structure that is at least 50 mole % hydrocarbon or dimethylsiloxane. In some embodiments, the carrier consists essentially of a compound or blend of compounds that has a chemical structure that is at least 50 mole % hydrocarbon or dimethylsiloxane. In various embodiments, the hydrocarbon compounds include alkyl, alkenyl, or alkynyl moieties, or a mixture thereof; linear, branched, or cyclic moieties, or a mixture thereof; aliphatic, or aromatic moieties, or a mixture thereof; and in embodiments is a blend of two or more such hydrocarbon compounds. "Dimethylsiloxane" means a repeating unit consisting of

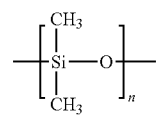

In various embodiments, the dimethylsiloxane is a linear or cyclic compound or a blend thereof, wherein n in the structure shown above is at least 3. Where the dimethylsiloxane is linear, the chain termination is hydrogen, hydroxyl, alkyl, aryl, or alkaryl. In embodiments, the chemical structure is about 50 mole % to 100 mole % hydrocarbon or dimethylsiloxane, or about 60 mole % to 99 mole % hydrocarbon or dimethylsiloxane, or about 70 mole % to 98 mole % hydrocarbon or dimethylsiloxane, or about 80 mole % to 95 mole % hydrocarbon or dimethylsiloxane, or about 90 mole % to 99 mole % hydrocarbon or dimethylsiloxane. In some embodiments, the carrier includes at least one compound or blend of compounds that has a chemical structure that is at least 50 mole % hydrocarbon. In some embodiments, the carrier consists essentially of a compound or blend of compounds that has a chemical structure that is 50 mole % to 100 mole % hydrocarbon, or about 60 mole % to 99 mole % hydrocarbon, or about 70 mole % to 98 mole % hydrocarbon, or about 80 mole % to 95 mole % hydrocarbon, or about 90 mole % to 99 mole % hydrocarbon, or about 95 mole % to 99 mole % hydrocarbon, or about 98 mole % to 100 mole % hydrocarbon.

In some embodiments, a suitable carrier includes petrolatum or consists essentially of petrolatum. Petrolatum (Merkur; mineral jelly; petroleum jelly; CAS No. [8009-03-8]; EINECS No. 232-373-2) is a purified mixture of semisolid saturated hydrocarbons having the general formula $C_nH_{2n+2}$, and is obtained from petroleum sources. The hydrocarbons consist mainly of branched and unbranched chains although some cyclic alkanes and aromatic molecules with alkyl side chains may also be present. Petrolatum is manufactured from the semisolid residue that remains after the steam or vacuum distillation of petroleum. This residue is dewaxed and/or blended with stock from other sources, along with lighter fractions, to give a product with the desired consistency. Final purification is typically performed by a combination of high-pressure hydrogenation or sulfuric acid treatment followed by filtration through adsorbents. A suitable antioxidant is added in some cases.

The rheological properties of petrolatum are determined by the ratio of the unbranched chains to the branched chains and cyclic components of the mixture. Petrolatum contains relatively high amounts of branched and cyclic hydrocarbons in contrast to paraffin, which accounts for its softer character. It has been shown by both rheological and spectrophotometric methods that petrolatum undergoes a melting phase transition onset between 23° C. and 40° C., depending on the specific blend of compounds in the mixture. Because petrolatum is a mixture, the phase transition occurs over a broad range, often between about 25° C. and 65° C., or about 30° C. and 60° C., or about 35° C. and 60° C. In embodiments, petrolatums have cone penetration of above 100 dmm and less than 275 dmm (ASTM D937).

Animal studies have shown petrolatum to be nontoxic and noncarcinogenic in both subcutaneous and oral dosing. Petrolatum is a GRAS material, is included in the U.S. FDA Inactive Ingredients Guide, and is accepted for use in food applications in many countries worldwide.

In some embodiments, a suitable carrier includes or consists essentially of a petrolatum-like material that is sourced from vegetable matter. Such materials are described, for example, in U.S. Pat. No. 7,842,746. The vegetable based petrolatum-like materials are made from hydrogenated polymerized vegetable oils, such as hydrogenated blown oils or hydrogenated copolymerized oils. The petrolatum-like materials are formulated to have a targeted range of properties and thus are suitably formulated to have melting transition onset of between about 23° C. and 40° C., as well as water contact angle to the surface of 90° or greater, measured according to ASTM D7334-08, and/or solubility in water of less than 1 wt % at 25° C., either alone or in a blend with one or more additional components.

In some embodiments, the carrier is characterized by the substantial absence of hydrophilic compounds, wherein "substantial" means, in this context, either that the presence of any hydrophilic compounds is not sufficient to reduce the water contact angle of the carrier to below 90°, or that the presence of any hydrophilic compounds is not sufficient to increase the water solubility of the carrier to more than 1 wt % at 25° C. In other embodiments, the carrier is characterized by the substantial absence of hydrophilic compounds. The nature and chemical structure of "hydrophilic compounds" is not particularly limited but includes any compound that, when added to the carrier, causes the water contact angle of the carrier to decrease, or the water solubility of the carrier to increase, or both. Surfactants, humectants, superabsorbents, and the like are examples of hydrophilic compounds that are added, in some embodiments, to the carrier for example to increase compatibility with a substrate, scavenge water from the carrier during processing, or some other purpose.

In embodiments, components included in the carrier are waxes, polymers, nucleating agents, oils, solvents, water scavengers, desiccants, adhesion promoters, antifouling agents, thermal or oxidative stabilizers, colorants, adjuvants, plasticizers, crosslinkers, or two more thereof. Components are not generally limited in nature and are dictated by the particular end use of the cyclodextrin compositions and treated substrates, further within the boundaries for the carrier properties set forth above.

In some embodiments, waxes are employed in the carrier. Waxes are hydrophobic compounds having melting points, or melting transition onsets, of over 40° C., for example between about 40° C. and 200° C., or between about 50° C. and 170° C., or between about 60° C. and 150° C., or between about 70° C. and 120° C. Hydrophobic means having solubility in water of less than 1 wt % at 25° C. Suitable waxes include paraffin wax, animal waxes, vegetable waxes, mineral waxes, synthetic waxes, bayberry wax, beeswax, microcrystalline wax, stearyl dimethicone, stearyl trimethicone, ethylene-α-olefin copolymers, $C_{18}$-$C_{45}$ olefins, and ethylene or propylene oligomers and short chain homopolymers as well as copolymers thereof. In some embodiments, the wax is a nucleating agent that improves the solidification "set time" of the carrier upon cooling, if the cyclodextrin composition is heated e.g. for blending or in order to coat it on a substrate. Nucleating agents include short chain polyolefin waxes of ethylene, propylene, or both, that are polymerized using Fischer-Tropsch catalysts or other specialized catalysts in order to induce high density (over 0.95 g/cm$^3$) and high crystalline content in the solid wax.

In some embodiments, oils are included in the carrier. Oils are hydrophobic compounds that are liquids at 25° C. Hydrophobic means having solubility in water of less than 1 wt % at 25° C. In some embodiments, the oil is a hydrocarbon or silicone oil; in other embodiments the oil is a plant oil such as peanut oil, walnut oil, canola oil, linseed oil, and the like. In some embodiments, the oil is a "drying oil", that is, the oil reacts with oxygen in the atmosphere to form crosslinks. In embodiments, one or more oils are added to the carrier at about 0.1 wt % to 50 wt % of the weight of the carrier, or about 0.5 wt % to 25 wt % of the weight of the carrier, or about 1 wt % to 10 wt % of the weight of the carrier.

In some embodiments, a combination of one or more of a polymer, a wax, petrolatum, and an oil are employed, together with one or more additional components to form the carrier meeting the criteria for melting transition onset and hydrophobicity as set forth above. In some embodiments, a wax and an oil, petrolatum and a wax, petrolatum and an oil, or a combination of a wax, petrolatum, and an oil are advantageously employed to form the carrier meeting the criteria for melting transition onset and hydrophobicity as set forth above. In other embodiments, a wax or petrolatum alone meet the criteria for melting transition onset and hydrophobicity as set forth above.

In some embodiments, water scavengers are included in the carrier. A water scavenger is a compound that is soluble or dispersible in the carrier, and is available to react preferentially with water molecules such that it effectively acts to scavenge ambient moisture from airborne humidity during standard processing conditions including admixing and application of the composition to a substrate. The amount of water scavenger added should be a minimum amount to react with ambient moisture during processing. This is because, during some intended uses of the cyclodextrin composition, water is required to facilitate release of the complexed compound into the environment. Thus, an amount of water scavenger should be provided in the cyclodextrin composition that is quickly depleted once a substantial amount of water vapor or liquid water is encountered. Examples of water scavengers suitably employed in the cyclodextrin compositions of the invention include various ortho esters and hexamethyldisilazane. In embodiments, about 1 wt % or less of the water scavenger based on the total cyclodextrin composition weight is added to the carrier, for example about 0.01 wt % to 1 wt % of the carrier or about 0.05 wt % to 0.5 wt % of the carrier.

In some embodiments, desiccants are employed in the carrier. In other embodiments, desiccants are employed elsewhere in conjunction with the treated substrates. For example, in some embodiments where the cyclodextrin inclusion complex is 1-MCP/c/α-CD, desiccants are useful to scavenge water from the interior of an enclosed volume into which a respiring produce material is expected to generate an excess of the desired amount of water needed for release of 1-MCP. In some embodiments, "excess water" means sufficient water vapor that 100% relative humidity is exceeded and liquid water is condensed within the enclosed volume. The effects of excess water are described in more detail below. Desiccants are also added, in some embodiments, directly to the interior of a treated container, or to a treated laminate separately from the cyclodextrin composition itself; however, in some embodiments, the desiccant is added directly into the carrier for convenience and/or efficiency. Examples of desiccants that are suitably employed include silica gel, activated charcoal, calcium sulfate, calcium chloride, montmorillonite clay, and molecular sieves. The amount of desiccant incorporated within the carrier is not particularly limited and is selected based on the particular end use, that is, amount of ambient humidity or liquid water expected in the end use, whether the application involves an enclosed volume, partially enclosed volume, or an unenclosed volume, and the like. In general, the amount of desiccant is selected to be about 0.001 wt % to 99 wt % based on the total weight of the cyclodextrin composition, or about 0.1 wt % to 50 wt % based on the total weight of the cyclodextrin composition, or about 1 wt % to 10 wt % based on the total weight of the cyclodextrin composition.

In embodiments, the cyclodextrin composition is formed by admixing the carrier with the cyclodextrin inclusion complex. In some such embodiments, the admixing is carried out at an elevated temperature, which in this context means a temperature greater than 20° C. In some such embodiments, the admixing is carried out under dry conditions. In this context, "dry" means the carrier, and any gaseous environment surrounding the carrier during processing and formation of the cyclodextrin composition, has less than 250 ppm of water, for example about 0.01 ppm to 250 ppm water, or about 0.1 ppm to 200 ppm water, or about 1 to 100 ppm of water. In some embodiments, the gaseous environment has less water than the carrier due to the ease of providing a dry gaseous environment as will be appreciated by the skilled artisan. In some embodiments, both elevated temperature and dry conditions are employed. The elevated temperature employed in the mixing is less than 90° C. when the inclusion complex is 1-MCP/c/α-CD, because 90° C. is the onset temperature triggering loss of 1-MCP from the inclusion complex. In some embodiments where 1-MCP is not the complexed compound, i.e. where the complexed compound is a fragrance or antimicrobial compound or set of compounds, a temperature above 90° C. is employed. The elevated temperature is employed to provide ease of mixing, due to the lowered viscosity of the carrier. In the case of 1-MCP/c/α-CD, the mixing is carried out between 20° C. and 90° C., or between about 30° C. and 80° C., or between about 40° C. and 75° C., or between about 60° C. and 75° C.

In embodiments, dry conditions are employed in connection with both the carrier and the surrounding environment during the admixing of the cyclodextrin composition. The surrounding environment includes, in various embodiments, air, nitrogen, argon, $CO_2$, or any other gas selected and includes a partial vacuum insofar as adsorbed water remains present e.g. on vessel surfaces. In some embodiments, the amount of water present in the carrier at 20° C. is between about 10 and 50 ppm of free water (water not taken up by a scavenger or a desiccant), or about 10 ppm to 80 ppm of free water at 30° C., or about 10 ppm to 200 ppm of free water at 50° C. In some embodiments, the surrounding gaseous environment includes about 4 ppm to 17 ppm water at 20° C., or about 7 ppm to 30 ppm water at 30° C., or about 10 ppm to 45 ppm water at 40° C., or about 15 ppm to 70 ppm water at 50° C.

In embodiments, the amount of cyclodextrin inclusion complex employed in the cyclodextrin composition is about 0.001% by weight to 25% by weight of the composition, or about 0.01% by weight to 10% by weight of the composition, or about 0.05% by weight to 5% by weight of the composition. The amount of cyclodextrin inclusion complex included in a particular formulation is selected based on the volume of the surrounding environment and the concentration of complexed compound desired in the environment, in conjunction with the permeability of the carrier to water, permeability of the carrier to the complexed compound, and presence of a second substrate if the treated substrate is a treated laminate. Criteria informing this selection are described in greater detail below.

In some embodiments where the treated substrate is a treated laminate, one or both of the first or second substrates includes one or more desiccants. In some such embodiments the desiccants are embedded in, or adhered to, the one or more substrates. In some such embodiments, one of the first or second substrates is a liner, that is, a removal substrate; in some such embodiments the desiccant is employed along with the liner to exclude water during storage and/or shipping. The liner is removed upon arrival of the treated substrate to its use destination, whereupon atmospheric moisture is available to trigger release of the complexed compound present in the cyclodextrin complex. The desiccant is attached to the liner in such a manner that it remains substantially attached to the liner when the liner is removed from the treated substrate.

Substrates usefully employed to form the treated substrates of the invention include any substrate suitable for disposition of the cyclodextrin composition on at least a portion of a surface thereof. In some embodiments, the substrate surface is the surface of a plate, film, or sheet and thus is substantially planar and well suited for continuous industrial coating operations. In other embodiments, the cyclodextrin composition is disposed on a non-planar substrate surface or an irregular substrate surface to form a treated substrate. In some embodiments, the substrate is a container. Suitable substrates include cellulosic and other natural and synthetic biomass-based substrates, as well as synthetic petroleum-based thermoplastic polymeric films, sheets, fibers, or woven, felted, or nonwoven fabrics, and composite materials including one or more thereof. Some examples of substrates usefully employed to form treated substrates, including treated containers and treated laminates, include paper, paperboard, cardboard, cartonboard such as corrugated cardboard, coated paper or cardboard such as extrusion coated paper or cardboard, chipboard, nonwoven, felted, or woven fabrics, wood, netting, wood/thermoplastic composites, glass, metals, polyvinyl halides such as poly(vinyl chloride) (plasticized and unplasticized) and copolymers thereof; polyvinylidene halides such as polyvinylidene chloride and copolymers thereof; polyolefins such as polyethylene, polypropylene, copolymers thereof, and morphological variations thereof including LLDPE, LDPE, HDPE, UHMWPE, metallocene polymerized polypropylene, and the like; polyesters such as polyethylene terephthalate (PET) or polylactic acid (PLA) and plasticized variations thereof; polystyrene and copolymers thereof including HIPS; polyvinyl alcohol and copolymers thereof; copolymers of ethylene and vinyl acetate; and the like. Blends, alloys, composites, crosslinked versions thereof, and recycled versions thereof are also useful in various embodiments. Two or more layers of such substrates are present in some embodiments as multilayer films or carton constructions. In some embodiments, the substrates are substantially continuous. In some embodiments the substrates are permeable, porous, microporous, perforated, meshed, foamed (open- or closed-cell) nonwoven fabrics, or are netting.

The substrates contain, in some embodiments, one or more fillers, stabilizers, colorants, and the like. In some embodiments the substrates have one or more surface coatings thereon. In some embodiments the substrate has a surface coating thereon prior to coating the cyclodextrin composition. Surface coatings include protective coatings such as wax, acrylic polymer, vinyl acetate/ethylene copolymer and ethylene/vinyl chloride copolymer coatings, and the like; coatings to render surfaces printable; coatings to render otherwise permeable substrates impermeable; adhesive coatings; primers; tie layer coatings; metalized or reflective coatings; and the like. The type and function of surface coatings are not particularly limited within the scope of this disclosure; likewise the manner in which the surface coatings are applied is not particularly limited. In various embodiments where a surface coating will be exposed to an enclosed or partially enclosed volume within a produce package, the surface coating is subsequently coated with the cyclodextrin composition.

In some embodiments, the substrate is polyethylene extrusion coated recyclable paperboard, corrugated cardboard, or carton board packaging, for shipment of produce. Printed paperboard or corrugated cardboard packaging ranges from bulk bins to specialized display cartons. The extrusion coated surface provides an opportunity to dispose a cyclodextrin composition thereon.

In some embodiments the substrate is pretreated with a plasma or corona treatment prior to disposing the cyclodextrin composition thereon. Such surface treatments are well known in the industry and are often employed in the industry to modify the surface energy of substrates, for example to improve wetting or adhesion of coatings or printed materials to the surface of a substrate. Such surface treatments are likewise useful in some embodiments to improve wetting and adhesion of the cyclodextrin compositions to the substrate.

In some embodiments, the substrate is treated with a primer prior to disposing the cyclodextrin composition thereon. In some such embodiments films and sheets of thermoplastics used as substrates are obtained or purchased already pre-coated with a primer; a wide variety of such films and sheets are available in the industry and are targeted for improving adhesion of various types of coatings thereto. In some embodiments a plain film or sheet is coated "in line" with a primer. A plethora of such coatings and technologies are available and one of skill will understand that primer coatings are optimized for each application and for the composition to be disposed thereon. Some examples of primer compositions suitably disposed between the substrate surface and the cyclodextrin compositions include polyethyleneimine polymers such as polyethyleneimine, alkyl-modified polyethyleneimines in which the alkyl has 1 to 12 carbon atoms, poly (ethyleneimineurea), ethyleneimine adducts of polyaminepolyamides, and epichlorohydrin adducts of polyaminepolyamides, acrylic ester polymers such as acrylamide/acrylic ester copolymers, acrylamide/acrylic ester/ methacrylic ester copolymers, polyacrylamide derivatives, acrylic ester polymers containing oxazoline groups, and poly (acrylic ester)s. In embodiments, the primer composition is an acrylic resin, a polyurethane resin, or mixture thereof.

An alternative method to treat or "prime" materials is via a glow discharge using either corona or atmospheric plasma. Both methods are typically used in an air atmosphere but other gases or gas mixtures can also be used and may include, and not limited to, oxygen, nitrogen, argon, helium, carbon dioxide, ammonia, water vapor, etc. The glow discharge treatment has the ability to "clean" material surfaces by removal of contaminants and to create polar moieties on surfaces. In some embodiments, such treatments promote adhesion of disposed materials thereto, uniformity of disposed coatings, or both. Examples of corona and plasma systems are those available from Enercon Industries (www.enerconind.com), Vetaphone (www.vetaphone.com), and Plasmatreat (www. plasmatreat.com). Advantages of corona and plasma treatment include: a) there is no need to add another chemical to the substrate, b) there is no need for drying or post curing of the substrate, c) glow discharge is a highly efficient process from gas utilization efficiency, and d) such processes are well aligned with sustainability guidelines regarding product, occupational and environmental safety.

In some embodiments where the cyclodextrin composition includes an olefinic inhibitor, the substrate is a sheet or film that is formed into a container suitable to hold produce within an enclosed space, a partially enclosed space, or an unenclosed space. In other embodiments the substrate is a sheet or film that is converted into coupons, strips, tabs, and the like for the purpose of insertion into an otherwise untreated container. In still other embodiments, the substrate is a treated laminate. In some embodiments, the treated laminate is permeable to the olefinic inhibitor on a first side thereof and is impermeable to the olefinic inhibitor on a second side thereof. In some embodiments, the substrate is a treated laminate that is permeable to water on at least a first side thereof. In some embodiments coupons, strips, tabs, and the like are labels that are adhesively applied to produce or a container. In some such embodiments, the coupons, strips, tabs, and the like are labels that are further printed with one or more indicia. The cyclodextrin composition is present, in various embodiments, on any surface that is directly or indirectly exposed to the produce; the exposure is within an enclosed space, a partially enclosed space, or an unenclosed environment. One of skill will appreciate that the amount of cyclodextrin inclusion complex in the cyclodextrin composition, the composition of the carrier, and the amount of cyclodextrin composition disposed in the vicinity of the produce will be varied in response to the substrate employed, type of produce, enclosed vs. unenclosed nature of the environment surrounding the produce, and the expected temperature and amount of water vapor encountered during use.

In some embodiments where the cyclodextrin composition includes an olefinic inhibitor, the cyclodextrin composition is directly disposed on produce, for example as a continuous or discontinuous coating, or as part of an adhesive or in printed characters on a printed or reverse printed produce label. In such embodiments, all or a portion of the coating or label contains the cyclodextrin composition.

In some embodiments, the treated substrate is incorporated within a personal care product. For example, a cyclodextrin composition having a cyclodextrin inclusion complex of a fragrance compound or an antimicrobial compound is used to form a treated fiber. The treated fiber is incorporated into a nonwoven sheet that is then formed into a wipe, a diaper, a feminine protection article, or the like. In another example, a cyclodextrin composition having a cyclodextrin inclusion complex of a fragrance compound is used to form a treated laminate. The treated laminate is incorporated into a tape article. Such tape articles are useful for a personal hygiene article, for example. In some embodiments, the one of the substrates employed to form the laminate is a removable liner. Upon removal of the liner, the fragrance is released slowly. Such removable-liner tape articles are useful for household fragrance release, for example to mount on a wall, or on a cat litter box, or near a diaper pail. In some embodiments, the liner is sectioned so that removal can be sequential, or two or more sections are removed at once, depending on the preference of the end user.

Because of the low temperature, dry conditions that are employed to form the articles, a high yield of the antimicrobial or fragrance properties are retained in the treated substrates when the end user triggers the start of the release of the selected complexed compound from the cyclodextrin composition. Similarly, in the case of 1-MCP or another olefinic inhibitor, a high yield of olefinic inhibitor is retained in the treated substrates after processing.

In embodiments, the yield of cyclodextrin complex on the treated substrate is at least 95 wt % of the weight of the cyclodextrin complex added to the carrier, for example about 95 wt % to 100%, or about 96 wt % to 99.99 wt %, or about 97 wt % to 99.9 wt %, or about 98 wt % to 99 wt %, or about 98 wt % to 100%, or about 98 wt % to 99.99 wt %, or about 99 wt % to 99.9 wt %, or about 99 wt % to 99.99 wt % of the cyclodextrin complex added to the carrier. The exact percent yield will depend on the temperature of processing vs. the inherent equilibrium of the cyclodextrin inclusion complex—including the volatility of the complexed compound, and the amount of water present during the processing, both in the carrier and in the surrounding environment.

Treated laminates include constructions having a cyclodextrin composition disposed between a first major surface of a first substrate and a second major surface of a second substrate. The second substrate is the same or different from the first substrate. In some such embodiments, the first or second substrate is the substrate from which a container is formed. In such embodiments, the cyclodextrin composition is generally not in direct contact with e.g. the interior of a treated container, or with produce, or other items; that is, it is disposed substantially between the first and second substrates. In some embodiments where the cyclodextrin composition includes an olefinic inhibitor, at least one of the first and second substrates is permeable to water, and at least one of the first and second substrates is permeable to the olefinic inhibitor. In some such embodiments, the first substrate is permeable to the olefinic inhibitor and the second substrate is impermeable to the olefinic inhibitor. In some such embodiments, the first substrate is permeable to water vapor and the second substrate is impermeable to water vapor. In some such embodiments, the second substrate is permeable to water vapor and the first substrate is impermeable to water vapor.

3. Methods of Making the Treated Substrates

In some embodiments, the cyclodextrin compositions are disposed onto the surface of a substrate by a coating technique. Coating is accomplished using several known coating technologies available in the industry. In some embodiments coating is accomplished without employing elevated temperatures, that is, by employing ambient temperatures of a processing facility. In other embodiments, the temperature during disposing is between about 20° C. and 90° C., or between about 40° C. and 80° C. In some embodiments, coating is carried out under dry conditions, employing conditions that are the same or substantially similar to the dry conditions described above.

Useful coating techniques employed to coat the cyclodextrin compositions include, for example, die coating, slot coating, curtain coating, flood coating, gap coating, notch bar coating, wrapped wire bar drawdown coating, dip coating, brush coating, spray coating, pattern coating such as rotogravure coating, and print coating employing printing technologies such as flexographic printing, inkjet printing, lithographic printing techniques, letterset printing, and screen printing. Viscosity of the cyclodextrin composition, the shape and composition of the substrate or produce, and the desire to coat the entirety vs. a portion of a surface dictates which of the known coating technologies are useful to coat the cyclodextrin compositions. For example, die coating, slot coating, notch bar coating, and the like are usefully employed to coat the entirety of a substantially planar web of substrate, whereas in embodiments where only a portion of a surface is to be coated, or coating onto a formed container or onto produce is desirable, one or more spray, dip, or print coating technologies is desirably employed. In some embodiments where a specific portion of a substrate is to be coated, or where a patterned coating is desired, print coating or rotogravure coating is desirably used.

We have found that flexographic printing techniques are particular well suited for use in conjunction with the cyclodextrin compositions to deliver a highly precise and reproducible amount of cyclodextrin composition to a substrate. Where the substrate is a sheet or film, great cost efficiency is realized by employing large scale continuous flexographic printing of the cyclodextrin compositions. The rheological profile of the carrier employed in the cyclodextrin compositions is surprisingly well suited for this production method; and the hydrophobic nature of the selected carrier material protects the cyclodextrin inclusion complex from ambient water vapor that results in premature loss of the complexed compound. Where the complexed compound is 1-MCP, prevention of premature loss is of critical importance for large scale production. This is because where large amounts of 1-MCP are released, as is potentially the case in a large scale production scenario, the risk of autopolymerization is maximized. The autopolymerization of 1-MCP is known to be a violent, explosive reaction and must therefore be avoided. Further, is has been established that the onset temperature for loss of 1-MCP from 1-MCP/c/α-CD is 90° C. The ability to coat (print) the cyclodextrin composition containing 1-MCP/c/α-CD under dry conditions and at temperatures below 90° C. thus provides a safe means for large scale production. Other complexed compounds have characteristic onset temperatures of release, and the low temperatures employed in both forming and printing the cyclodextrin compositions of the invention are advantageous from the standpoint of delivering maximum yield of intact cyclodextrin inclusion complex to the intended substrate for use in the intended application. Flexographic printing also imparts the ability to deliver a highly precise and reproducible amount of cyclodextrin composition to a substrate, resulting in the maximum efficiency in terms of controlled release. Where the complexed compound is 1-MCP, this further translates to a more consistent distribution of 1-MCP in and around the produce, which in turn results in consistent preservation of the produce. Consistency in distribution of 1-MCP is a recognized problem in the industry that is easily solved using this approach. Finally, we have found that the hydrophobic carrier employed in the approach provides a predictable, reproducible, and consistent rate of release of the complexed compound during use and in the presence of water vapor or liquid water or both. Again, where the complexed compound is 1-MCP, the consistency is critical for solving the known problem of inconsistent 1-MCP distribution within groupings of produce, wherein in employing the approaches of the prior art, some produce within a container would appear to receive a sufficient amount of 1-MCP, and thus be preserved satisfactorily, and some would appear to receive either an insufficient amount of 1-MCP or none at all.

Flexography is a form of relief printing wherein a liquid ink is applied to an elastomeric surface, called a plate, on which the image is raised above the rest of the surface as a 3D positive relief. It is a web-based, continuous process that employs a series of cylinders, or rolls, to transfer ink to a substrate. In a typical flexographic process, a flexographic ink is applied in a uniform layer to the raised portions of the flexographic plate mounted on a cylinder, or roll, via an ink metering cylinder, called an anilox roll, and the ink is then transferred from the flexographic plate onto a continuously moving substrate via a series of rolls. The inks typically employed are either quick drying, such as a solvent based ink, or are radiation curable.

Flexography is used most commonly to apply graphic images or labeling to substrates such as packaging films or sheets in a continuous process, wherein conversion of the films or sheets is carried out after the printing. A wide range of substrates are conveniently and easily addressed in flexographic printing. Examples of substrates commonly addressed include a wide range of thermoplastic films such as polyethylene, polypropylene, polyester, and nylon films, foils, coated and uncoated paper, paperboard, and corrugated board. In some instances, even nonwoven webs are printed using flexographic printing techniques. Ease of use makes flexography an ideal printing method for many packaging and labeling uses.

Another feature of flexographic printing is that the technique lends itself to application of multiple layers. While only one color can be applied per flexographic plate for example, three, four, or more plate printing combinations are easily built into flexographic lines in serial fashion in order to build full color images in a single pass. Further, application of a laminated top film layer or a printed top layer, such as a UV curable clearcoat, for protective purposes is easily incorporated within a flexographic operation. One lamination approach easily incorporated into the flexographic process involves application of a UV curable adhesive to a first, flexographically printed substrate, followed by application of a transparent second substrate to the adhesive and curing of the adhesive that is accomplished by UV transmission through the second substrate. In some such embodiments, the application of the adhesive is also accomplished by a flexographic printing process.

Additionally, the techniques employed to make flexographic plates lend themselves readily to providing a precise amount of material to a substrate in a repeating pattern or a continuous pattern. Further, flexographic printing is achievable at very high speeds, up to about 2000 ft/min or about 600 meter/min, with high precision. Finally, digital, direct-to-plate engraving using laser imaging to remove flexographic plate layers has enabled the use of higher durability materials than were accessible using the traditional photopolymer imaging methods of plate generation, which further improves the already economically favorable profile of large scale flexographic printing processes by greatly extending plate life. The laser imaging method retains the tight tolerances, measured in tenths of thousandths of an inch, of the photopolymer imaging method; these tolerances are necessary for high quality, precision flexographic printing.

Chill rolls used in the flexographic printing industry provide web cooling after the ink is transferred to the substrate. In such embodiments, after printing, the web is passed over a chill roll, wherein contact with the chill roll is made with the major side opposite the printed side. Cooling the web retards ink smearing and helps reduce web temperature before the next printing station, in order to assure proper registration of the next printed layer. This is of particular importance in operations where heat, whether added to remove solvent or produced by UV curing of inks, has insufficient time to dissipate during high speed continuous runs.

The flexographic printing industry is divided into two sectors, delineated by the printing press width: wide web presses, over about 470 mm wide, that address applications such as flexible packaging, sacks, pre-print and disposables; and narrow web presses, below 470 mm wide, that are used both for shorter runs and for narrow web applications such as pressure sensitive labels, paperboard cartons, corrugated packaging, and narrow web flexible packaging.

While any of the substrates listed in the sections above are suitably addressed in flexographic printing operations, one area addressed commonly and conveniently in flexographic applications is flexible packaging. Flexible packaging is formed from substrates of ten millimeters or less wherein the shape of the substrate is readily changed. Common flexible packaging substrates include, for example, polyolefin and polyester films wherein printing is carried out on one or both major surfaces of a substantially flat web as it is unwound from a roll source. A large proportion of printing and labeling of flexible packaging, including bar code labeling for example, is carried out using flexographic processes. An industry shift from rigid to flexible packaging has also resulted in an increase in the use of flexographic printing and labeling of packaging materials for fresh produce, snack foods, drugs, surgical and medical products, pet food, agricultural products, and industrial chemicals.

The cyclodextrin compositions are suitably applied to any substrate that can be printed using flexographic printing processes. Since the carrier employed in the cyclodextrin compositions has a kinematic viscosity of less than 30 $mm^2/s$ at 100° C., the flexographic printing is suitable carried out by heating the cyclodextrin compositions to temperatures of 90° C. and below, for example between about 60° C. and 80° C., or between about 50° C. and 70° C. At these temperatures, we have found that the cyclodextrin compositions print cleanly and precisely using standard flexographic conditions including high line speed. For example, the line speeds achievable using flexographic printing of the cyclodextrin compositions at temperatures below 90° C. are about 10 meters per minute (m/min) to 600 m/min. In embodiments the minimum line speed is about 30 m/min, or about 40 m/min, or about 50 m/min, or about 60 m/min, or about 75 m/min, or about 100 m/min, or about 150 m/min, or about 200 m/min, or about 250 m/min, or about 300 m/min, or about 400 m/min, wherein the maximum line speed is about 600 m/min in any selected embodiment.

Further, the cyclodextrin compositions are easily kept dry while in a sealed container awaiting flexographic printing on a production line. In this way, long term storage issues encountered in some applications, that is, the need to keep the cyclodextrin composition dry, is obviated. Thus, the premature loss of the complexed compound is avoided and high yield of the cyclodextrin inclusion complex is realized. As is discussed above, this is advantageous for all cyclodextrin compositions, but is of critical importance in the case of low boiling olefinic inhibitors and in particular in the case of 1-MCP, due to its tendency to autopolymerize.

In some embodiments, after printing and downweb in a flexographic printing press, a chill roll is employed to reduce the temperature of the cyclodextrin composition on the substrate. In some such embodiments, the chill roll is employed at a temperature wherein the contact time of the chill roll with the substrate is sufficient to lower the temperature of the cyclodextrin composition to at or below the melting transition onset of the carrier. Use of the chill roll is advantageous where the flexographic process, or another coating process, involves elevated temperatures to lower the viscosity of the cyclodextrin composition during the disposing on the substrate, but insufficient cooling otherwise occurs between the disposing and a subsequent step in processing the treated substrate. In some embodiments, lowering the temperature of the cyclodextrin composition to below the melting temperature of the carrier prevents the running, transferring, or smearing of the cyclodextrin composition in subsequent printing or other processing steps. In embodiments, the chill roll is set to a temperature of about −100° C. to 10° C., or about −80° C. to 0° C. Agents employed to lower the temperature of the chill roll are known to those having skill, but include, for example, ice, dry ice, and combinations thereof of with solvents, salts, and the like; or a liquid such as water, an alcohol, ethylene glycol or another glycol, a mixture of one or more thereof, or another liquid or mixture, such as an anti-freeze mixture, that is circulated between the chill roll and a refrigeration apparatus.

In some embodiments, after the cyclodextrin composition is disposed on the substrate to form the treated substrate, the treated substrate is further processed to form a treated laminate. In such embodiments, the treated substrate is a treated first substrate. The treated first substrate is further laminated with a second substrate to form the treated laminate. In some such embodiments, the second substrate is a thermoplastic film coated with a pressure sensitive adhesive, wherein the treated laminate is formed by contacting the first substrate on the printed side thereof with the second substrate on the adhesive side thereof. In some embodiments, pressure is further applied to the treated laminate, for example by passing the treated laminate through a nip roll, in order to more firmly affix the second substrate to the first substrate. In such embodiments, the second substrate is not particularly limited in terms of the material employed, and the material may be selected, for example, to provide targeted permeability to water, the complexed compound, or both. In some such embodiments the second substrate includes, by way of example, paper, a nonwoven, or a thermoplastic film; in some embodiments the thermoplastic film is porous, microporous, permeable, impermeable, or perforated.

In other embodiments, a treated laminate is formed by applying a UV curable (polymerizable and/or crosslinkable) adhesive, also referred to as a laminating adhesive, directly to the first substrate after flexographically printing the cyclodextrin composition thereon, and a second substrate is wet laminated to the uncured adhesive by applying the second substrate employing a nip. The adhesive is then cured by irradiating through the second substrate, typically very close to the nipped wet lamination point. Thus, in such embodiments, it is necessary that the second substrate be at least partially transparent to the UV wavelength range employed in the curing process. In some embodiments, a laminating adhesive coating thickness of about 2 μm to 15 μm is applied via flexographic printing, using about 100 to 2000 lines/cm. The UV lamp is mounted proximal to the nip point where the film is laminated to prevent separation or air pockets from forming in the laminated substrate. The skilled artisan will appreciate that the adhesive cure conditions are adjusted to provide sufficient and optimal cure; line speed, bulb energy (mJ per unit of area), and thickness of the adhesive layer are common variables, for example. In some embodiments, a curable adhesive is cured via electron beam (e-beam) in similar fashion to the UV curing process, but employing an e-beam instead of UV light. In such embodiments, the need to add a photoinitiator is obviated.

The desired amount of the cyclodextrin composition disposed per unit of area of a treated substrate, whether by flexographic printing or by some other technique, is not particularly limited within the scope of the composition. The desired amount per unit area of the cyclodextrin composition is a function of both the thickness of a layer disposed on the substrate, and whether or not the layer is a continuous or discontinuous layer. Continuous layers are commonly deposited by coating techniques such as knife coating, curtain coating, spray coating, and the like; discontinuous or patterned layers are commonly deposited by printing techniques such as gravure, screen, flexographic, or inkjet printing. While it is not necessary to limit the thickness of either a continuous or a discontinuous coating to a single thickness, in practicality this is most often selected for economy. While the thickness of the cyclodextrin composition disposed on the substrate is limited in some embodiments by the technique employed in disposing it, the thickness is further selected based on the amount of cyclodextrin inclusion complex in the cyclodextrin composition, the inherent equilibrium ratio of the cyclodextrin inclusion complex with uncomplexed compound, the permeability of the carrier to the uncomplexed compound, the permeabilities of the first and second substrates if the treated substrate is a treated laminate, the surface area selected to receive the cyclodextrin composition, and the amount of the uncomplexed compound that is desirably present in the environment surrounding the treated substrate. Where the compound is an olefinic inhibitor, the amount of the uncomplexed compound that is desirably present in the environment surrounding the treated substrate, also referred to herein as the "effective amount", is based on the type of produce selected for olefinic inhibitor exposure, the volume of the enclosed, partially enclosed, or unenclosed space surrounding the produce, and the expected conditions of temperature and humidity. It is a feature of the cyclodextrin compositions that such amounts are selected with ease, wherein the amounts of olefinic inhibitor released are predictable, reproducible and consistent.

In some embodiments, the thickness of a continuous or discontinuous cyclodextrin composition layer, disposed on a treated substrate, is between about 0.01 micrometer (μm) and 5 millimeter (mm) thick, or between about 0.1 μm and 1 mm thick, or between about 0.5 μm and 0.05 mm thick; however, as stated above, the thickness of a continuous or discontinuous cyclodextrin composition layer is not particularly limited and is selected for one or more criteria including, for example, the selected technique of disposing the cyclodextrin composition, the amount of cyclodextrin inclusion complex included in the cyclodextrin composition, the rheological profile of the composition, the total surface area selected for the disposing, and the continuous or discontinuous nature of the coating.

In embodiments, the treated substrates include discontinuous coatings of the cyclodextrin compositions disposed on the substrates, wherein the discontinuous printed coating covers between about 0.1% and 99% of the available surface area of the substrate, or about 1% to 90%, or about 2% to 80%, or about 5% to 70%, or about 10% to 60%, or about 20% to 50% of the available surface area of a substrate; in some embodiments, the discontinuous printed coating covers between 0.1% and 99% of the available surface area of the substrate in any range therein in intervals of 0.1% of the surface area, for example between 55.3% and 58.9%, or between 40.3% and 40.4%, or between 0.5% and 1.0%, or between 0.8% and 22.7%; it is a feature of the invention that the amount of cyclodextrin composition deposited on the surface of the substrate is easily controlled to such an extent by employing the methods of the invention to print discontinuous patterns of the cyclodextrin compositions on a variety of substrates as described herein.

In some embodiments, the cyclodextrin complex is blended with a printable media to form a printable media composition, wherein the printable media composition is printable using flexographic printing. Printable media compositions include, consist essentially of, or consist of a cyclodextrin complex and a printable media. A printable media is a material or blend of materials that is a solid at or below about 30° C. and has a kinematic viscosity of less than 30 mm²/s at 100° C. Any material or blend of materials meeting these requirements is suitable as a printable media for flexographic printing and suitable for use in a printable media composition. The printable media composition includes at least the printable media and a cyclodextrin complexed with a complexed compound. The complexed compounds useful in the printable media compositions are the same as those described above, that is, an olefinic inhibitor, a fragrance, or an antimicrobial molecule; blends of cyclodextrin complexes are also suitably employed in the printable media compositions.

In embodiments of the printable media composition where the complexed compound is 1-MCP, it is necessary that the printable media have a kinematic viscosity of less than 30 mm$^2$/s at 90° C., and preferable that the printable media be provided and maintained in a dry condition during addition of the cyclodextrin complex to form the printable media composition as well as during printing of the printable media composition onto one or more substrates using flexographic printing.

Examples of useful printable media include, by way of non-limiting examples, lower molecular weight polyalkylene oxides, including linear and branched adducts thereof, end-capped adducts thereof, and copolymers thereof such as polyethylene oxide-polypropylene oxide block copolymers; hydrocarbon, fluorocarbon, or silicone waxes; fatty acids and esters thereof; salt hydrides; and blends of these, as well as blends of these with one or more additional components.

In various embodiments, additional components usefully included in the printable media are any of the materials disclosed above as components of the hydrophobic carrier. Thus, petrolatum or materials having similar properties thereto, polymers, nucleating agents, oils, solvents, water scavengers, desiccants, adhesion promoters, antifouling agents, thermal or oxidative stabilizers, colorants, adjuvants, plasticizers, crosslinkers, or two more thereof are included in various embodiments of the printable media. Additional components are not generally limited in nature and are dictated by the particular end use of the printable media compositions and treated substrates formed by printing the printable media compositions onto one or more substrates, further within the property boundaries for the printable media properties set forth above.

In some embodiments, waxes are employed as the printable media, either alone or in a blend with other components. Waxes useful in the printable media are hydrophobic or hydrophilic compounds generally having low molecular weights and having melting points, or melting transition onsets, between about 40° C. and 200° C., or between about 50° C. and 150° C., or between about 50° C. and 120° C., or between about 50° C. and 100° C. Suitable waxes include polyalkylene oxide waxes, paraffin wax, animal waxes, vegetable waxes, including hydrogenated polymerized oils such as those described in U.S. Pat. No. 7,842,746, mineral waxes, synthetic waxes, bayberry wax, beeswax, microcrystalline waxes, alkyl dimethicones, alkyl trimethicones, lower ethylene-α-olefin copolymers, $C_{18}$-$C_{45}$ olefins, and ethylene or propylene oligomers and short chain homopolymers as well as copolymers thereof. In some embodiments, the wax is a nucleating agent that improves the solidification "set time" of the printable media upon cooling, if the printable media composition is heated e.g. for blending or in order to coat it on a substrate. Nucleating agents include short chain polyolefin waxes of ethylene, propylene, or both, that are polymerized using Fischer-Tropsch catalysts or other specialized catalysts in order to induce high density (over 0.95 g/cm$^3$) and high crystalline content in the solid wax.

In some embodiments, microcrystalline waxes are employed in the printable media. In embodiments, microcrystalline waxes have melting points ranging from 54° C. to about 102° C. They have needle penetration of above 3 dmm and less than 100 dmm (ASTM D1321). Viscosities are higher than 5 cP at 100° C. In some embodiments, the microcrystalline wax is petroleum based. In other embodiments, the microcrystalline wax is vegetable based, for example a hydrogenated polymerized oil such as a vegetable based wax described in U.S. Pat. No. 7,842,746. Also described in U.S. Pat. No. 7,842,746 are vegetable based petrolatum-like materials, which are similarly useful in the printable media as a component thereof.

In some embodiments, oils are included in the printable media. Oils are hydrophobic or hydrophilic compounds that are liquids at 25° C. and in some embodiments are combustible and have viscosities greater than about 5 cP at 25° C. In some embodiments, the oil is a synthetic hydrocarbon or silicone oil; in other embodiments the oil is a plant oil such as peanut oil, walnut oil, canola oil, linseed oil, and the like. In some embodiments, the oil is a "drying oil", that is, the oil reacts with oxygen in the atmosphere to form crosslinks. In some embodiments, the oil is an essential oil.

In embodiments, a printable media composition is printed onto a substrate using flexographic printing to form a printed substrate. The term "substrate" is defined above; "printed substrate" means a substrate having a printable media composition disposed thereon by flexographic printing. In all other respects, a printed substrate is the same as a treated substrate as that term is used elsewhere herein; and the printed substrate is used in the same applications and in the same way as the treated substrates as described elsewhere herein. It is an advantage of flexographic printing methodology that discontinuous patterns, such as discrete "islands" containing the printable media compositions, are easily formed using flexographic printing of the printable media compositions.

In embodiments, the printed substrates include discontinuous coatings of the printable media compositions disposed on the substrates, wherein the discontinuous printed coating covers between about 0.1% and 99% of the available surface area of the substrate, or about 1% to 90%, or about 2% to 80%, or about 5% to 70%, or about 10% to 60%, or about 20% to 50% of the available surface area of a substrate; in some embodiments, the discontinuous printed coating covers between 0.1% and 99% of the available surface area of the substrate in any range therein in intervals of 0.1% of the surface area, for example between 55.3% and 58.9%, or between 40.3% and 40.4%, or between 0.5% and 1.0%, or between 0.8% and 22.7%; it is a feature of the invention that the amount of printable media composition deposited on the surface of the substrate is easily controlled to such an extent by employing the methods of the invention to print discontinuous patterns of the printable media compositions on a variety of substrates as described herein.

In some embodiments, the printed substrate is a printed laminate, wherein the printable media composition is printed onto a first substrate, and a second substrate is disposed over the printable media composition after the printing. In all other respects, the printed laminate is the same as a treated laminate, as that term is used elsewhere herein; and the printed laminate is used in the same applications and in the same way as the treated laminates as described elsewhere herein.

In some embodiments, the printed substrate is a printed container, wherein the term "container" is defined above; "printed container" means a container having a printable media composition disposed thereon by flexographic printing. In embodiments the printed container includes a printed substrate or a printed laminate. In some embodiments, the printed container is formed from a printed substrate or a printed laminate. In some embodiments the printed container includes a printed substrate as an integral part of the container. In some embodiments, a container is a substrate, and the printable media composition is printed thereon to form the printed container. In some embodiments, a printed substrate or a printed laminate is added to a container to form the printed container. In all other respects, the printed container is the same as that term is used elsewhere herein; and the printed container is used in the same applications and in the same way as the treated containers as described elsewhere herein.

4. Methods of Using the Treated Substrates

The treated substrates, treated laminates, and treated containers are usefully employed in a number of applications. Where the cyclodextrin composition includes a fragrance, the treated substrates, treated laminates, and treated containers are usefully employed in household fragrance applications including household perfume release, vacuum cleaner bag fresheners, odor releasing wipes, cat litter box fresheners, garbage can fresheners, car perfume release articles, and the like. Where the cyclodextrin composition includes an antimicrobial, the treated substrates, treated laminates, and treated containers are usefully employed in flexible food packaging films, labels, disposable work surface films, personal care products, comestible containers, bedding, wipes, medical products such as bandaging, medical drapes, and medical clothing for slow release of antimicrobial compounds. In some embodiments, the treated substrates, treated laminates, and treated containers are usefully formed to contain both fragrance and antimicrobial compounds for slow and controlled release, since in certain articles a combination thereof is advantageous.

Where the cyclodextrin composition includes an olefinic inhibitor, the treated substrates, including treated laminates and treated containers, are usefully employed in the inhibition of maturation or ripening of produce. In some embodiments, the treated substrates are usefully included within the enclosed volume of packaged produce. In embodiments, the treated substrate is arranged such that the cyclodextrin composition contacts the interior atmosphere of the enclosed volume surrounding one or more produce items, the enclosed volume being provided by the container. The type and conformation of the produce container is not particularly limited; any bag, box, punnet, carton, tub, cup, pallet, bag, transportation interior (e.g. truck interior), etc. that defines an enclosed space usefully employs the treated substrates. Ambient humidity, humidity from produce respiration, added liquid water or water vapor, or a combination of two or more thereof provide the necessary water that triggers release of the olefinic inhibitor from the cyclodextrin inclusion complex.

In other embodiments, the treated substrate is arranged such that the cyclodextrin composition contacts the atmosphere surrounding a partially enclosed or unenclosed volume near one or more produce items, or within or nearby a partially enclosed or unenclosed container. In some such embodiments, the container is a treated container, but in other embodiments the container is not a treated container and the treated substrate is provided outside the container but in proximity thereto. In such embodiments, the proximity is simply determined by whether an effective concentration of the olefinic inhibitor is provided in the atmosphere surrounding the produce, taking into account the amount of cyclodextrin composition, amount of liquid water or water vapor present in the atmosphere, the degree of partial enclosure, and the type of produce. The type and conformation of the produce container is not particularly limited; any bag, box, carton, punnet, tub, cup, pallet, bag, transportation interior (e.g. truck interior), building area, gated outdoor area, etc. that defines a partially enclosed space or an unenclosed space usefully employs the treated substrates. Ambient humidity, humidity from produce respiration, added liquid water or water vapor, or a combination of two or more thereof provide the necessary water that triggers release of the olefinic inhibitor from the cyclodextrin inclusion complex.

The surface area and thickness of the cyclodextrin composition exposed to the interior of a produce container is selected to provide a suitable atmospheric (gaseous) concentration of the olefinic inhibitor to the enclosed space such that the useful life of the produce is optimized. The selection process is discussed in more detail below. Factors affecting the provision of the optimum atmospheric concentration of olefinic inhibitor include the type of produce being addressed, the amount of cyclodextrin inclusion complex in the cyclodextrin composition, the amount of cyclodextrin composition present on the treated substrate, the inherent equilibrium ratio of the cyclodextrin inclusion complex with uncomplexed olefin inhibitor, the permeability of the carrier to the olefinic inhibitor, the permeability of the substrate or substrates to the olefinic inhibitor, the viscosity or coating thickness requirements of the technique employed to coat the cyclodextrin composition, the volume of the enclosed, partially enclosed, or unenclosed space surrounding the produce that will be addressed, and the amount of liquid or gaseous water expected within the same volume, included ambient humidity and water vapor generated by transpiration of the plant material.

In some embodiments, the treated substrate is simply a sheet or film bearing a coating, such as a slot coating or flexographically printed coating, of the cyclodextrin composition; in other embodiments the treated substrate is a treated laminate. In some such embodiments the amount of complexed compound required for a particular application is estimated based variables such as the desired level of the complexed compound in the atmosphere, the volume of atmosphere to be addressed, and the amount of water amount expected. Then based on the total coated volume of cyclodextrin composition per unit area of the treated substrate, the substrate is divided—for example, by cutting the treated substrate—to a selected size that delivers the correct amount of cyclodextrin composition. In other embodiments, uniform sections are pre-cut and one, two, or more sections are selected to provide a total selected coated amount of cyclodextrin composition.

In such calculations, the value of delivering a targeted coating amount to the targeted volume is realized. Certain embodiments described above are particularly advantageous in delivering a precisely measured amount of cyclodextrin composition to an enclosed, partially enclosed, or unenclosed volume, as well as enabling delivery of an easily varied amount of cyclodextrin composition to a target container. For example, flexographic printing is well understood to deliver precise and easily varied volumes of material to substrates over an easily varied surface area of a variety of substrates. Another advantage of using printing techniques to deliver the cyclodextrin compositions is that printing is easily incorporated into a production assembly line setup for packaging materials and other industrially and commercially useful formats and thus provides a convenient and economical means for building a delivery vehicle for release of complexed compounds from the cyclodextrin compositions, whether applied directly on a container, or on a label, a closure, or within a laminate applied to a container, on a treated substrate added to a container, within a treated laminate included in an open area, or the like.

In some embodiments where the complexed compound is an olefinic inhibitor, the substrate used to make a treated substrate employs an additional means to control the amount of water (vapor and/or liquid) enclosed within a container while further in the presence of the produce material. While the amount of water in a package's enclosed space is of concern from the standpoint of release of an olefinic inhibitor from the cyclodextrin compositions of the invention, it is well known that very high levels of moisture in a package containing produce material is also separately detrimental to certain moisture sensitive produce (berries, citrus, lettuce, mushrooms, onions, and peppers, for example). Excess moisture triggers various physiological disorders in some postharvest fruits and vegetables, shortening shelf life and quality. In particular, liquid water in the form of condensation on produce material surfaces hastens spoilage and considerably shortens storage life. In some embodiments, internal humidity controllers (humectants and desiccants) are incorporated into porous sachets, within the substrate of the invention, or even within the cyclodextrin compositions themselves in conjunction with a treated substrate. In embodiments, humidity controllers help maintain optimum in-package relative humidity (about 85% to 95% for cut fruits and vegetables, for example), reduce moisture loss from the produce material itself, and/or prevent buildup of excess moisture in headspace and interstices where microorganisms can grow. The amount of olefinic inhibitor incorporated within the packaging structure will be different in packaging having excess water as contrasted by lower humidity packaging of low transpiration postharvest products. Therefore, to operate the technology a number of factors (chemical and biological) will be considered to manufacture optimum packaging structures and bulk shipping containers for different groups of postharvest products.

In embodiments where the complexed compound is an olefinic inhibitor, treated substrates are useful in embodiments where modified atmosphere packaging (MAP), equilibrium modified atmosphere packaging (EMAP), or controlled atmosphere packaging (CAP) is employed. The objective in MAP is to provide a desired atmosphere around produce by providing a sealed container having controlled permeability to oxygen and carbon dioxide, resulting in an improvement in produce quality when compared to air storage. Typically, the permeability of the container changes with temperature and partial pressures of each gas exterior to the container. The objective in CAP is to displace some or all of the atmospheric air composition (78% $N_2$, 21% $O_2$) within the container with e.g. carbon dioxide or nitrogen or a blend of two or more gases in a desired proportion. A number of patents set forth various features of MAP and CAP. U.S. Pat. No. 7,601,374 discusses both approaches and also references a substantial list of other patents issued for various MAP and CAP technologies. It will be appreciated that the cyclodextrin compositions find further utility in conjunction with MAP, CAP, or technologies that combine features of both approaches. In some embodiments, the cyclodextrin compositions are employed directly, wherein the MAP, EMAP, or CAP substrates are employed as treated substrates; in other embodiments, treated substrates are added to the MAP, EMAP, or CAP packages, e.g. as inserts.

MAP is a useful approach for maintaining improved flavored fruits and vegetables by minimizing development of off-flavors due to fermentative metabolism or odor transfer from fungi or other sources. MAP is recognized to improve resistance to postharvest stresses, decay and other plant disorders. An 'active package' having a modified atmosphere integrated with the controlled release of an olefinic inhibitor as delivered by the cyclodextrin compositions of the invention will improve the quality of fresh-cut fruits and vegetables for consumers including single-serve, ready-to-eat packaging and containers for vending machines. In an exemplary embodiment of the invention, MAP or CAP is used in conjunction with the treated substrates of the invention for large polyethylene bags employed to packaging pallets of cartons, wherein the cartons contain fresh produce. Such pallet-size bags are widely employed for shipment of pallets of produce, supported in cartons; the bags are employed for the purpose of enclosing the produce in a modified or controlled atmosphere during shipping. In some such embodiments, the bags, the paperboard (e.g. polyethylene extrusion coated paperboard) cartons, labels on the cartons or the bag, a treated insert, or a combination of two or more thereof include a treated substrate of the invention.

EMAP is a method to help prolong the shelf life of fresh produce by optimizing the in-package equilibrium atmosphere. This is achieved by modifying the permeability of the packaging film. Film micro-perforation is one way to regulate the equilibrium concentrations of $O_2$ and $CO_2$. Micro-perforated films are apertured films or otherwise rendered porous, by puncturing or by stretching a film made from a mixture of a thermoplastic material and particulate filler. These films permit the transfer only by molecular gas/vapor diffusion and block the transfer of liquid. Examples of microporous or micro-perforated films include FRESHHOLD® film, available from River Ranch Technology, Inc. of Salinas, Calif.; P-PLUS® film, available from Sidlaw Packaging of Bristol, Great Britain and described in U.S. Pat. Nos. 6,296,923 and 5,832,699; and films from Clopay Plastic Products Co. of Mason, Ohio described in U.S. Pat. Nos. 7,629,042 and 6,092,761.

Additionally, in embodiments where the complexed compound is an olefinic inhibitor, treated substrates are useful in embodiments where gas permeability of non-perforated and nonporous films is modified by simply manufacturing films of different thicknesses or using the selectivity of hydrophilic films produced from segmented block copolymers, and employing these materials as substrates in conjunction with the cyclodextrin compositions. Segmented block copolymers or multi-block copolymers consist of alternating flexible soft segments and crystallizable rigid segments. The properties of segmented block copolymers are varied by changing the block lengths of the flexible (soft) and rigid segments. Rigid and flexible segments are thermodynamically immiscible and, therefore, phase separation occurs. The rigid segments crystallize and form lamellae in the continuous soft phase. Rigid segments can contain ester, urethane or amide groups, while the flexible segments are usually polyesters or polyethers—poly(ethylene oxide) (PEO) and/or more hydrophobic poly(tetramethylene oxide) (PTMO). In breathable film, the gas vapor is transported mainly through the soft phase; selective gas permeability depends on the density of the hydrophilic groups in the polymer, the relative humidity, and the temperature.

In embodiments where the complexed compound is an olefinic inhibitor, treated substrates are useful in embodiments where specialized and selectively permeable substrates are employed. One example of a selectively permeable substrate is BreatheWay® packaging, currently used in conjunction with fresh-cut produce marketed by Apio, Inc. of Guadalupe, Calif. (www.breatheway.com; also see www.apioinc.com). BreatheWay® films are selectively permeable membranes that control influx of oxygen and outflux of carbon dioxide in order to provide adjusted $O_2/CO_2$ ratios to extend shelf life. The membranes are also temperature responsive. While such packaging provides improved $O_2/CO_2$ ratios for extending shelf life of respiring produce, it does not otherwise inhibit ripening of the produce. Examples of other suitable breathable hydrophilic films include PEBAX®, a thermoplastic polyamide manufactured by Total Petrochemicals USA, Inc. of Houston, Tex.; SYMPATEX®, a breathable hydrophilic polyether-ester block copolymer manufactured by SympaTex Technologies GmbH of Unterföhring, Germany; HYTREL®, a thermoplastic polyester elastomer manufactured by DuPont deNemours and Co. of Wilmington, Del.; and segmented polyurethanes such as ELASTOLLAN® (ELASTOGRAN®) and PELLETHANE®, supplied by Dow Chemicals of Midland, Mich. These polymers have a large, selective gas permeability range. The cyclodextrin compositions, in conjunction with such permeable membrane technology, represent a complete solution to extended shelf life of respiring produce.

It will be appreciated that the articles and applications described above benefit in a number of ways from the advantages offered by the compositions and methods described herein. The cyclodextrin inclusion complexes are easily formed and isolated using mild conditions wherein high yields of inclusion complex formation are realized. The cyclodextrin inclusion complexes are easily stored until added to a cyclodextrin composition. The cyclodextrin compositions are easily formed and coated using mild conditions. The cyclodextrin compositions are easily stored or can be formed and used in a production line. A variable and precise amount of cyclodextrin composition is easily and reproducibly added to a variety of substrates, and laminates and containers are easily addressed. A variety of easily implemented methods of delivering the cyclodextrin compositions are possible, and flexographic printing is a particularly useful methodology to deliver a variable and precise amount of cyclodextrin composition to a variety of substrates rapidly and economically. The treated substrates of the invention are useful in a wide variety of applications for slow and controlled release of the complexed compounds within the cyclodextrin inclusion complexes.

5. 1-Methylcyclopropene (1-MCP) as the Olefinic Inhibitor

In embodiments where the cyclodextrin inclusion complex includes the olefinic inhibitor 1-MCP, the effective amount of cyclodextrin composition disposed on the treated substrate is selected to provide an atmospheric (gaseous) concentration of 1-MCP to the enclosed, partially enclosed, or open volume surrounding the selected produce such that the useful life, or "shelf life", of the produce is extended over the shelf life of the produce in the absence of the cyclodextrin composition. An effective amount of 1-MCP in the environment within the enclosed, partially enclosed, or unenclosed surrounding the produce is between about 1 part per billion (ppb) to about 10 parts per million (ppm), or between about 5 ppb and 5 ppm, or between about 10 ppb and 3 ppm, or between about 50 ppb and 2 ppm, or between about 100 ppb and 1 ppm, or between about 25 ppb and 1 ppm, or between about 50 ppb and 500 ppb, or any intermediate range between 1 ppb and 10 ppm in any increment of 10 ppb, such as 10 ppb to 50 ppb, 100 ppb to 500 ppb, and the like; it is a feature of the invention that such ranges are realistically and accurately targeted using the cyclodextrin compositions.

In embodiments the 1-MCP cyclodextrin inclusion complex is formed with α-cyclodextrin; that is, 1-MCP/c/α-CD. A factor in addition to those factors mentioned above affecting 1-MCP release from 1-MCP/c/α-CD is the amount of water present in liquid or vapor form in the region immediately proximal to the treated substrate. This requires consideration of the amount of water released by respiring produce, and the amount of water retained within the package as that amount changes with plant respiration in the case of an enclosed or partially enclosed package that also includes the treated substrate.

In embodiments of the invention where 1-MCP/c/α-CD is employed in the cyclodextrin compositions and treated substrates of the invention, the treated substrate is exposed to an atmosphere within the enclosed volume, partially enclosed volume, or unenclosed volume that is proximal to one or more items of produce. This atmosphere must include an activating amount of water such that the 1-MCP/c/α-CD releases the 1-MCP into the vicinity of the produce at sufficient concentration to inhibit produce ripening or maturation of the produce. Water sources include ambient humidity, water vapor and/or liquid water from the respiration of the produce itself, or water vapor or liquid water added in a controlled amount in the vicinity of the cyclodextrin composition. In embodiments, the cyclodextrin composition, the substrate or substrates, or both are permeable to both 1-MCP and to water vapor to a sufficient degree to maintain a ripening or maturation inhibiting amount of 1-MCP in the vicinity of, that is, proximal to, the produce.

The water-facilitated release of 1-MCP from 1-MCP/c/α-CD is described in detail by Neoh, et al., *Carbohydrate Research* 345 (2010), 2085-2089. The Neoh researchers studied dynamic complex dissociation of 1-MCP/c/α-CD and observed that increasing humidity generally triggered 1-MCP complex dissociation in a predictable manner. However, the dissociation was greatly retarded at 80% relative humidity, presumably owing to collapse of the crystalline structure; then abrupt dissociation corresponding to complex dissolution was observed at 90% relative humidity. However, the researchers noted, as did present authors, that even at 100% relative humidity that less than 20% of the complexed 1-MCP is released. In fact, an average of less than one-fifth (~17.6%) of the total amount of complexed 1-MCP was dissociated at the end of the experiments while ~83.4% 1-MCP remained complexed.

In some embodiments, during distribution and storage of packaged produce, when storage temperature is between about 0° C. and 2° C., the relative humidity in an enclosed volume around the produce will be between about 50% and 100% due to normal water loss from produce respiration within an enclosed package volume. The increase in humidity within the enclosed volume of the package is sufficient, in embodiments, to release a portion of the 1-MCP from the 1-MCP/c/α-CD within an enclosed volume containing the cyclodextrin composition. In other embodiments, the humidity surrounding a treated container is increased by the addition of water in or around the container. In some such embodiments humidity is increased around produce by adding moisture via water mist, spray or steam during packaging, by controlling the humidity of the environment in the packaging location or within a storage facility, or by adding water to a container immediately prior to forming an enclosed volume surrounding the produce.

The importance of the relationship between water and 1-MCP dissociation from α-MCP/c/α-CD is of utmost importance in employing the technology because:
1) the amount of 1-MCP is regulated in the atmosphere surrounding fruits and vegetables on a country-by-country basis; and
2) the benefit (i.e., shelf life extension) derived from 1-MCP differs with exposure concentration for various types of produce material (see, e.g. Blankenship, S. M. and Dole, J. M., *Postharvest Biology and Technology* 28 (2003), 1-25); further, adverse effects to some produce materials are possible with excessive 1-MCP treatment concentrations.

In two examples of country-by-country regulation, the United States' Environmental Protection Agency (EPA) currently limits 1-MCP to a maximum of 1 ppm in air by authority of Section 408 of the Federal Food, Drug, and Cosmetic Act (FFDCA); and the European Commission Health and Consumer Protection Directorate and Member States of the European Food Safety Authority similarly regulates 1-MCP under its various directives, limiting 1-MCP levels to amounts ranging from 2.5 ppb v/v to 1 ppm v/v.

Thus, in embodiments, 1-MCP dissociation must be carefully managed within a container headspace by controlling both the total amount of 1-MCP incorporated within the container and the release of 1-MCP from the inclusion complex. Additionally, in embodiments, the amount of residual water inherently adsorbable or absorbable by the cyclodextrin compositions further affects 1-MCP dissociation. In embodiments, the hydrophilic nature of the cyclodextrin itself increases the compatibility of water with the cyclodextrin composition into which a cyclodextrin inclusion complex is incorporated.

In embodiments of the invention where the treated substrates employ 1-MCP/c/α-CD as the cyclodextrin inclusion complex, the amount of 1-MCP in the atmosphere that is required for a particular application is calculated based on several factors, as is discussed above; then the coating thickness and area coated (that is, the total coating volume) is varied based on the volume of the produce containing environment to be addressed, the enclosed, partially enclosed, or unenclosed nature of the environment to be addressed, concentration of 1-MCP/c/α-CD included in the cyclodextrin composition, and approximate fraction of 1-MCP/c/α-CD that is complexed (vs. uncomplexed α-CD) to arrive at the targeted atmosphere. Factors that must be considered in such a calculation include any humectants or desiccants within the container, the substrate, or the cyclodextrin composition itself; water and 1-MCP permeability/adsorbability/absorbability of the cyclodextrin composition, water and 1-MCP permeability/adsorbability/absorbability of the substrate (or substrates, in the case of a treated laminate), any controlled or modified atmosphere present within the container, and respiration rate of the targeted produce material.

For example, if an atmosphere containing 1 ppm of 1-MCP is required and a targeted enclosed volume is 1 liter, then assuming 100% 1-MCP complexation and an overall density of the cyclodextrin composition of 1 g/cm$^3$, a cyclodextrin composition containing 1.71 wt % α-cyclodextrin coated 12.7 μm thick in an area totaling 2 cm$^2$ would provide the targeted 1 ppm of 1-MCP to the enclosed volume in the presence of water vapor using Ideal Gas Law conversion. In embodiments, the targeted weight range of 1-MCP/c/α-CD is 25 micrograms to 1 milligram per 1 liter of enclosed volume. In such calculations, the value of delivering a targeted coating amount to the targeted enclosed volume is realized. Certain embodiments described above are particularly advantageous in delivering a precisely measured amount of 1-MCP to a selected volume, as well as enabling an easily varied amount of cyclodextrin composition to a target container.

As described above, the use of flexographic printing is well understood to deliver precise and easily varied volumes of material to substrates over an easily varied volume. We have demonstrated in the Examples below that this approach works well to deliver a precise and controlled amount of cyclodextrin composition to the targeted substrate, which in turn provides a reproducible and low level of release in the presence of water vapor.

6. Certain Additional Embodiments

The following definitions apply in relation to sections 1-5 above. The definitions in this section apply only to this section.

Device (for retarding plant spoilage) means "article" or "treated laminate" as defined in section 1, as determined by context.

Interior layer or exterior layer means the first or second substrate of the treated laminate of section 1.

Encapsulating agent means "carrier" as defined in section 1.

Carrier or complexing agent are broad terms that are employed as "cyclodextrin" is employed in section 1, that is, as a means to complex the active ingredient.

Active ingredient or active means "olefinic inhibitor" as defined in section 1.

Storage unit means "article" or "container" as defined in section 1, as determined by context.

Disclosed herein is a device for retarding plant spoilage which includes an exterior layer and a water vapor permeable interior layer with an encapsulating agent positioned between the exterior layer and the interior layer. The encapsulating agent encapsulates a carrier and an active ingredient associated with the carrier. The purpose of the active ingredient is to retard plant spoilage due to the presence of ethylene gas inside sealed storage units commonly used for storage and transport of plant material such as, for example, fruits and vegetable. These actives are meant to be released into the headspace of such storage units due to the water vapor that also resides within the headspace of the storage unit. The water vapor causes the active ingredient to be released from carrier with which it is associated thereby allowing the active ingredient to inhibit the effects of the ethylene gas within the headspace of the storage unit as ethylene is a known facilitator of plant ripening and spoilage. Some actives used to prevent such spoilage can be prematurely released due to exposure to, for example, the normal humidity of the surrounding air in the area in which it is stored prior to use. The encapsulating agent serves to protect the active ingredient from premature exposure to water vapor it may encounter prior to use yet within the headspace of the storage unit, the encapsulating agent will still permit the active ingredient and carrier to be contacted by the water vapor so as to release the active ingredient within the headspace to facilitate the retardation of the plant spoilage. To assist the contact of the active by the water vapor, it is desirable that at least the interior layer be permeable to water vapor and so it is desirable that the interior layer have a water vapor transmission rate greater than 3.0 g×mil/100 in$^2$×day.

In some applications, it may be desirable that the exterior layer resists permeation of water vapor to the interior space of the device. In such instances, it is desirable that the exterior layer have a water vapor transmission rate less than 3.0 g×mil/100 in$^2$×day.

To facilitate the functioning of the encapsulating agent, it is advantageous that the encapsulating agent be non-aqueous. Other desirable properties of the encapsulating agent are; that it have a melting point less than about 80° C., that it be a semi-solid at room temperature, and that it have a glass transition temperature (Tg) of about minus 200° C. to about 20° C.

Suitable encapsulating agents include animal waxes, vegetable waxes, mineral waxes, synthetic waxes, bayberry wax, beeswax, stearyl dimethicone, stearyl trimethicone, polyethylene, ethylene-alpha olefin copolymers, ethylene homopolymers, $C_{18}$-$C_{45}$ olefins and poly alpha olefins with ethylene-alpha olefin copolymers, ethylene homopolymers, $C_{18}$-$C_{45}$ olefins and poly alpha olefins being a preferred subset of this group.

Due to the fact that some active ingredients are gases in their natural state and unstable, it is often desirable that the carrier be a complexing agent capable of complexing with the active ingredient. Cyclodextrin is one carrier material that has been found to work particularly well and alpha-cyclodextrin has been found to work particularly well, especially when the active ingredient is 1-methyl cyclopropene.

The device containing the encapsulating agent along with the carrier and active ingredient is designed to be used inside a storage device for plant material. In some instances, it may be desirable for the exterior layer of the device to have an attachment means for attaching the exterior layer to another surface such as an inside surface of the storage unit. To protect the attachment means, it can optionally be covered with a peelable release strip which can be removed from the attachment means prior to its attachment to another surface. The interior layer is permeable to water vapor. To further protect the active ingredient within the interior space between the interior and exterior layers, the interior layer may be protected by a release liner which covers all or a portion of the exterior surface of the interior layer and which can be removed once the device is placed within the headspace of a storage unit. Thus, it is desirable that the release liner have a higher degree of resistance to water vapor than the interior layer. Alternatively stated, the release liner should have a lower water vapor transmission rate than the interior layer.

To further protect and encapsulate the encapsulating agent, the carrier and the active ingredient, at least a portion of the exterior layer and the interior layer of the device can be sealed to one another by a peripheral seal to prevent leakage of the encapsulating agent and the carrier from the device.

The storage unit in which the device is placed can comprise a sealed package layer which defines an interior space, which is also referred to as the headspace. The device can simply be placed inside the storage unit in such a manner that it is free to move about within the headspace or, as previously mentioned, it may be attached to an interior surface of the sealed package layer forming all or a portion of the storage unit.

To further integrate the device with the storage unit, in one embodiment the storage unit can comprise a sealed package layer which defines an interior space for storing plant material and the device can form at least a portion of the sealed package layer.

In any of the foregoing storage unit designs, it may be desirable for the unit to have means for opening and closing the storage unit.

Definitions Applying to this Section Only

The term "film" refers to a thermoplastic film made using a film extrusion process, such as a cast film or blown film extrusion process. The film can be a monolayer, or a multi-layer film or a laminate.

The term "water vapor permeable films" includes films, such as thermoplastic polymer-containing films, which permit the flow of water through open or inter-connected pores. The term includes films rendered porous by puncturing or aperturing, and films rendered porous by mixing polymer with filler, forming a film from the mixture, and stretching the film sufficiently to form liquid passages through the film.

The term "open-celled foam material" refers to a layer material made with the aid of a foaming process, in which the cells in the foam create open pores from one surface of the layer to the opposite surface. The term does not include foams which substantially block the flow of liquid water, such as closed-cell foam materials unless they have been apertured or otherwise modified to permit the transmission of water and/or water vapor from one surface of the foam to another surface of the foam.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "water vapor permeable" refers to a material present in one or more layers, such as a film, nonwoven fabric, or open-celled foam, which is porous, and which is water-permeable due to the flow of water in liquid or vapor form through the pores of the layer. The pores in the film or foam, or spaces between fibers or filaments in a nonwoven web, are large enough and frequent enough to permit leakage and flow of liquid and/or vaporous water through the layer. The term does not include films and other materials which block the transfer of water or water vapor.

The term "cyclodextrin compound" includes any compound which includes the cyclodextrin ring structure, including derivatives of cyclodextrins that maintain the ring structure. The ring structure may be that of an α-cyclodextrin compound (6 glucose units), a β-cyclodextrin compound (7 glucose units), a γ-cyclodextrin compound (8 glucose units), or a combination including compounds having one or more of these ring structures.

Product Forms and Applications

Figure 1A:
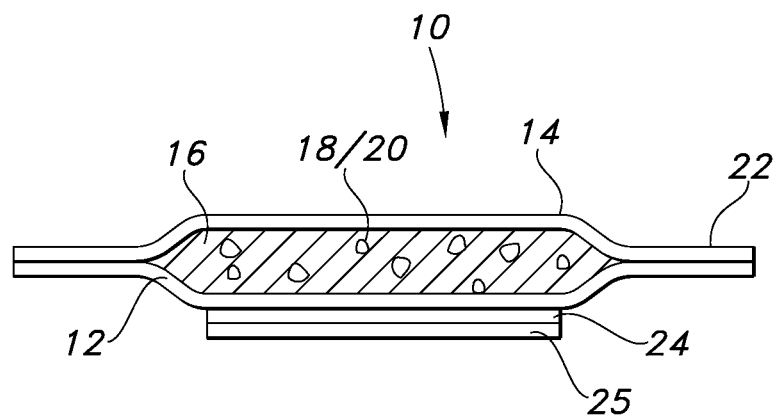
FIG. 1A is a cross-section of the article in FIG. 1 taken along line 1A-1A of FIG. 1.
Figure 2:
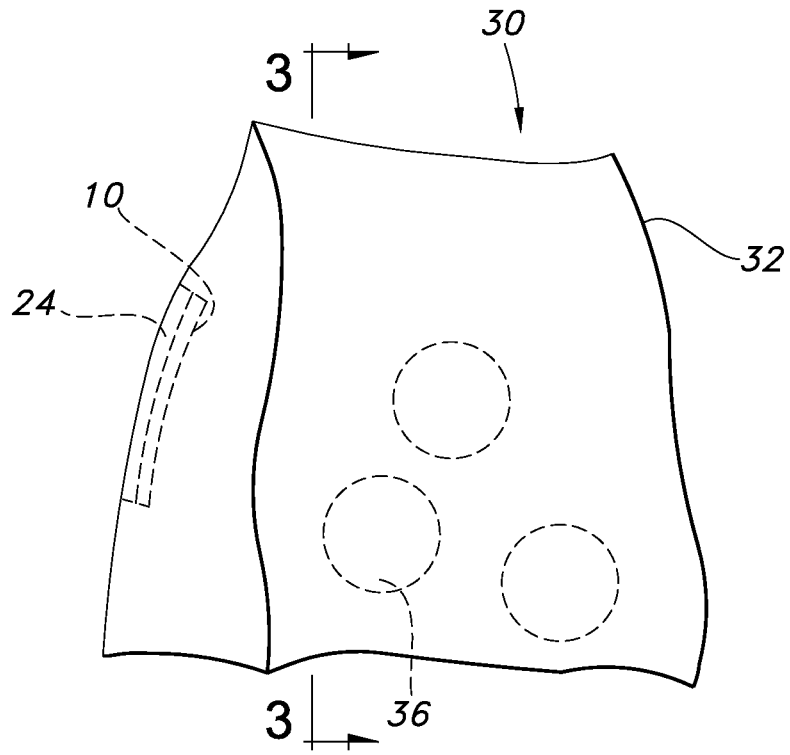
FIG. 2 is a perspective view of another article according to the present invention.
Figure 3:
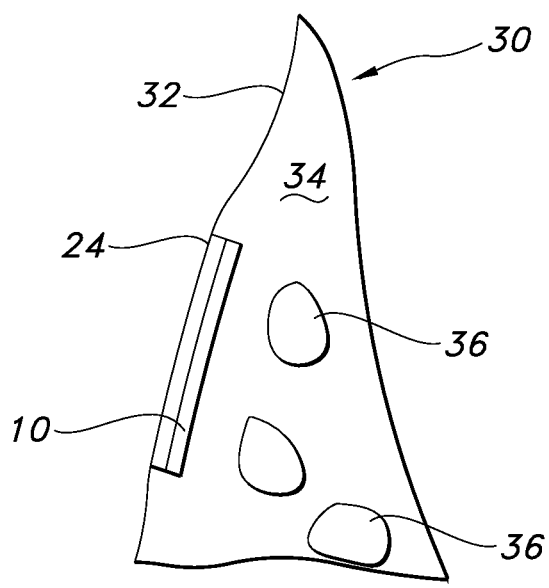
FIG. 3 is a cross-sectional side view of the article of FIG. 2 taken along line 3-3 of FIG. 2.

One embodiment of a device 10 for retarding plant spoilage is shown in FIGS. 1 and 1A of the drawings. Turning to FIG. 1, the device 10 includes an exterior layer 12, a water vapor permeable interior layer 14, an encapsulating agent 16, a carrier material 18 and an active ingredient 20. As will be explained in greater detail below, in many embodiments, it will be desirable that the exterior layer be water vapor impermeable. The active ingredient 20 is associated with the carrier material 18 and this combination is encapsulated within and coated by the encapsulating agent 16 and the combination of the encapsulating agent 16, the carrier material 18 and the active ingredient 20 are positioned between and contained by the exterior layer 12 and the interior layer 14. To contain these materials (16, 18 and 20), at least a portion of the exterior layer 12 and the interior layer 14 may be sealed to one another such as by a peripheral seal 22. In addition, optionally, an attachment means 24 such as a layer of adhesive or other bonding material may be applied to an exterior surface of the device 10 such as the exterior layer 12 or the interior layer 14 so that the device can be adhered to another surface such as the inside of a storage unit 30 as shown in FIGS. 2 and 3.

As explained in further detail below, in one embodiment, the encapsulating agent 16 is polyolefin wax (also referred to as petrolatum), the carrier material 18 is cyclodextrin and the active ingredient is 1-MCP which has been complexed with cyclodextrin.

In operation, the encapsulating agent 16, which is hydrophobic in nature, surrounds and coats the carrier 18 and active 20 thus protecting them from premature exposure to water and/or water vapor. However, as the device 10 is handled, water and/or water vapor can penetrate through the water vapor permeable interior layer 14 and come in contact with the carrier/active inside the device 10. Since cyclodextrin is hydrophilic, moisture condenses on it and through capillary action, moisture displaces 1-MCP from the cyclodextrin cavity. A detailed description of the mechanism and kinetics of the release of 1-MCP from cyclodextrin by contact with moisture can be found in the article entitled *"Dissociation characteristic of the inclusion complex of cyclomaltohexaose (α-cyclodextrin) with 1-methylcyclopropane in response to stepwise rising relative humidity"*, by Tze Leon Neoh, et al., Carbohydrate Research, 345 (2010), 2085-2089 which is incorporated herein by reference it its entirety.

As the plant package is handled, the device 10 inside the package will twist and flex by its own movement inside the package as well as by the contacting of the device 10 by the plant material inside the package, thereby exposing more of the encapsulated carrier/active to the water/water vapor inside the package and therefore releasing more of the active ingredient 20 into the headspace of the package.

Turning to FIGS. 2 and 3 there is shown a storage unit or package 30 which in this case is a plastic food storage bag such as is commonly used to store and sell individually-sized packages of perishable produce such a fruits and vegetables in grocery stores. The storage unit 30 includes a sealed package layer 32 which defines an interior space 34 and houses a perishable plant material 36. The airspace surrounding the plant material 36 is referred to in the industry as the headspace which is also referenced by element 34 and the two words are meant to be used interchangeably. It is this headspace 34 which contains the gases emitted by the plant material 36 including ethylene. The headspace 34 also contains oxygen and carbon dioxide.

As shown in FIGS. 2 and 3, the device 10 is located within the headspace 34 of the storage unit 30. The device 10 may simply be placed inside the headspace 34 along with the plant material 36 or it may be affixed to the interior surface of the storage unit 30 as by way of an attachment means 24 such as, for example, an optional adhesive layer 24 located on, for example, an exterior surface of the device 10 such as the exterior layer 12 shown in FIG. 1A. Alternatively, the attachment means 24 may be applied to an interior surface of the storage unit 30 and the exterior layer 12 of the device 10 may be adhered to the attachment means 24. Still further, if desired, the device 10 may be attached to the storage unit 30 by any other suitable attachment means such as by heat sealing or taping it to the storage unit 30.

Figure 4:
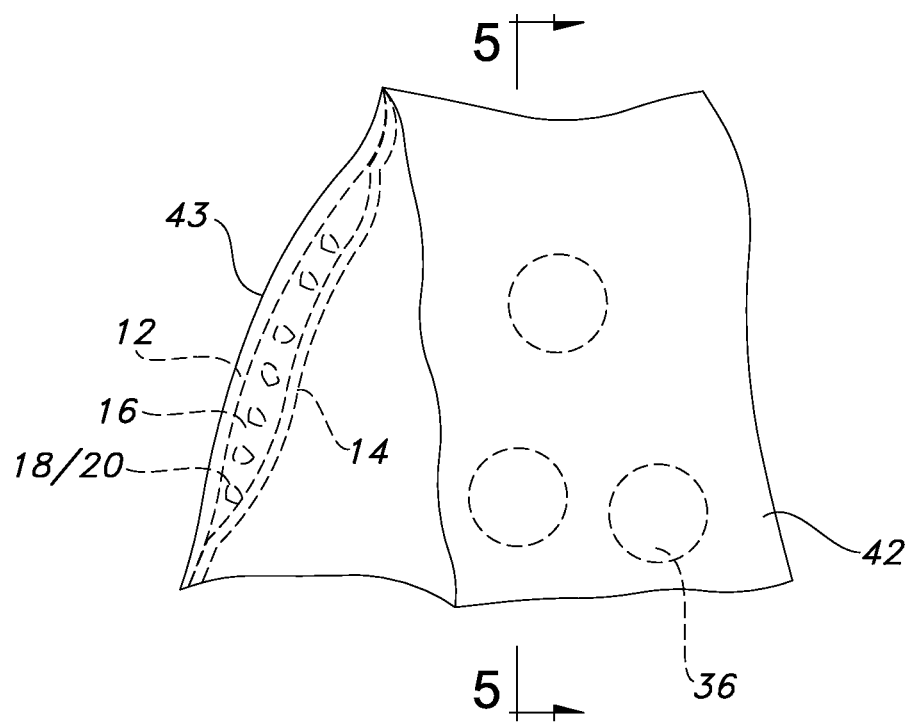
FIG. 4 is a perspective view of another article according to the present invention.
Figure 5:
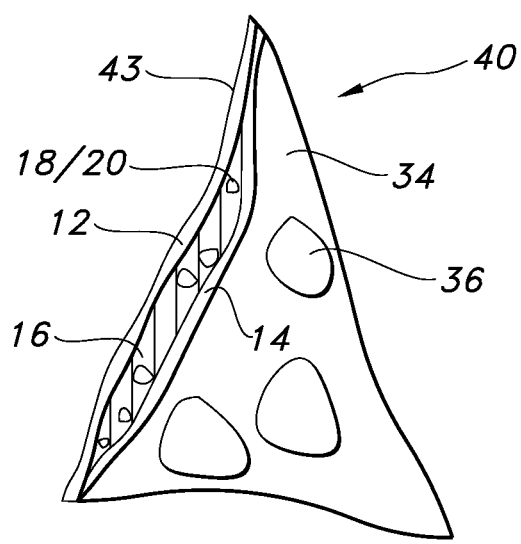
FIG. 5 is cross-sectional view side view of the article of FIG. 4 taken along line 5-5 of FIG. 4.

Turning to FIGS. 4 and 5, there is shown another storage unit 40. In this embodiment, all or a portion of the sealed package layer 42 may be formed of the device 10. As shown in FIGS. 4 and 5, one side 43 of the storage unit 40 is formed of the device 10 with the exterior layer 12 forming the exterior surface of the storage unit 40.

While the storage units 30 and 40 shown in FIGS. 2 through 5 are in the form of small individual packages for end-consumer use, it should be appreciated that the present invention can be scaled up or down to fit any suitable storage unit. Plant material such as fruit, vegetables and ornamentals such as flowers are subject to degradation from the point of initial harvesting until the end of the use cycle by the end-user. As a result, such items may be placed in and transferred to multiple storages units as part of this cycle. Thus, the present invention is intended to be used in any of such storage units.

Figure 6:
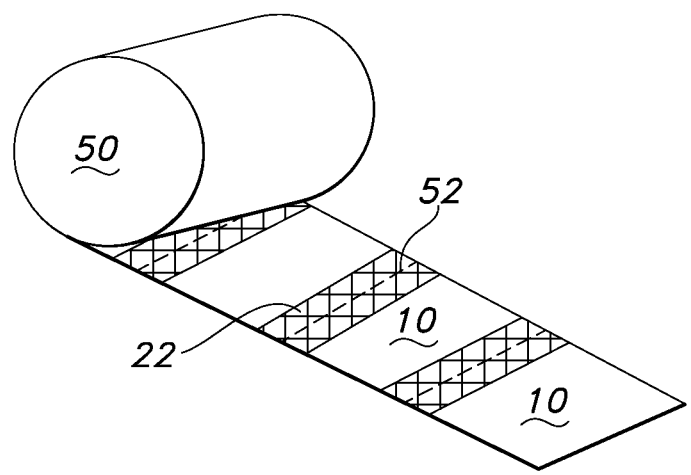
FIG. 6 is a perspective view of another article according to the present invention.

Referring to FIG. 6, individual devices 10 may be made in roll form 50 with perforations or other separation means 52 between the individual devices 10 so they can be separated from one another and be placed into individual storage units 30 (note shown). Alternatively, the perforations or other separation means 52 may be omitted and a cutting mechanism (not shown) may be used to cut and separate the individual devices 10 of the roll 50 by cutting through the peripheral seal 22 between individual devices 10.

Figure 7:
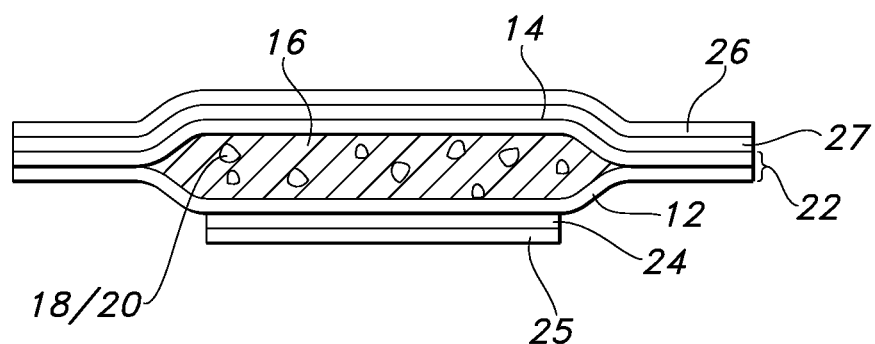
FIG. 7 is a cross-sectional side view of another article according to the present invention.

In the consumer area, smaller versions of these rolls 50 or stacks of individual, separate or folded devices 10 may be sold in packages for the consumer to use in conjunction with both disposable and re-useable food storage cartons such as sealable plastic bags and plastic containers with sealable lids. In such applications, whether in roll form or in individual stacks, the devices 10 may be provided with the aforementioned attachment means 24 located on the exterior surface of the exterior layer 12. See FIG. 7. As a result, it may be desirable to protect the attachment means 24, which in this example is an adhesive patch 24, with a peelable release strip 25 as shown in cross-section in FIG. 7. Such peelable release strips 25 are well known and commonly employ a paper or other substrate, at least one side of which typically has been coated with a release coating such as a layer of silicone which contacts the adhesive 24. Further, to protect the water vapor permeable interior layer 14, the exterior surface of the interior layer 14 may also be protected by a release liner 26 which can be peeled off the exterior surface of the interior layer 14 prior to use. See FIG. 7. The release liner 26 will typically have a layer of adhesive 27 or other suitable attachment means affixed thereto.

Figure 8:
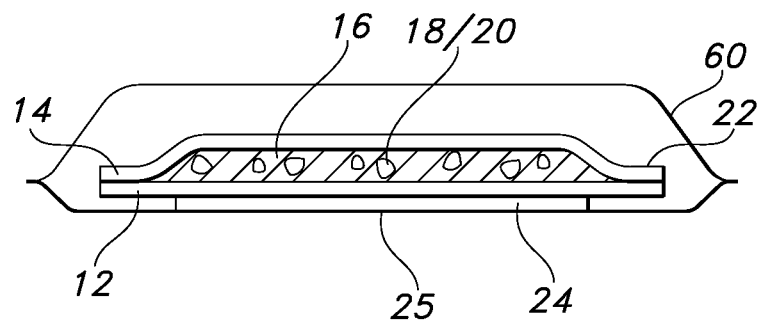
FIG. 8 is cross-sectional side view of another article according to the present invention.

In yet a further embodiment, the individual devices 10 may be wrapped and sealed in individual pouches 60, such as is shown in cross-section in FIG. 8, much like other products such as, for example, individually wrapped sanitizing wipes. In so doing, the devices 10 can be kept airtight and protected from premature exposure to water and water vapor prior to use. In this application, if an attachment means such as an adhesive layer 24 is used, it may once again be protected by a release strip 25 (not shown) or the interior surface of the pouch may act as the release strip 25.

In yet another embodiment (not shown), the present invention may be scaled to use in very large containers where large volumes of plant material are stored and transported such as in sea containers. In such applications, the container wall itself may serve as the exterior layer 12, the combination of encapsulating agent 16, carrier material 18 and active ingredient 20 may be applied to the interior wall in bulk form such as by brushing or spraying and then covered with an interior layer 14 which may be adhesively or otherwise attached or removably attached to the wall of the container which serves as the exterior layer 12. Alternatively, the encapsulating agent 16, carrier material 18 and active ingredient 20 may be impregnated into or coated onto another substrate such as a foam material or a fibrous nonwoven web such as a spunbond web or a staple fiber web which can in turn be secured between the exterior layer 12 and the interior layer 14.

Next a more detailed explanation of the various components of the device 10 will be undertaken.

Exterior Layer

The exterior layer 12 should resist transmission of water and/or water vapor into the interior portion of the device 10 between the exterior layer 12 and the interior layer 14 where the carrier material 18 and the active ingredient 20 are located. In applications where plastic films and bags are being used, it is desirable that the exterior layer 12 be made from polymers that employ desirable properties. Examples of such properties include that the material be flexible, transparent for viewing the condition of the package contents, haze-resistant, printable, sealable, puncture resistant and impermeable to water and water vapor and, optionally, the passage of gases such as oxygen, carbon dioxide and ethylene.

Any number of film-forming polymers may be used to form the exterior layer 12. Examples of film-forming polymers include, but are not limited to, polyolefins, polyolefin plastomer polymers (POP), ultra-low density polyethylene (ULDPE), linear low density polyethylene (LLDPE), low density polyethylene (LDPE), styrene-butadiene copolymers, ethylene vinyl acetate (EVA) and very low density polyethylene (VLDPE). It is desirable in some applications that the exterior layer 12 be impermeable to water and water vapor/moisture so that the active 20 is not prematurely released. This is particularly true when the exterior layer 12 forms all or a portion of the food storage unit 30 such as a plastic food storage bag or container. However, if the device 10 is to be used inside storage unit 30, it may be desirable to have the exterior layer 12 be permeable to water and water vapor/moisture. A measure of whether a film or other material is water vapor permeable or impermeable is by measuring its water vapor transmission rate or WVTR. This value can be determined in accordance with ASTM test method F1249-06 (Reapproved 2011) (at 38° C. and 100 percent relative humidity) which is incorporated herein by reference in its entirety. When it is desired that this layer 12 be water vapor impermeable, the layer 12 should have a WVTR less than 3.0 g×mil/100 in$^2$×day (1.18 g×mm/m$^2$×day) and desirably a WVTR of between about 0.5 g×mil/100 in$^2$×day (0.20 g×mm/m$^2$×day) and about 2.0 g×mil/100 in$^2$×day (0.79 g×mm/m$^2$×day). Note that multiplying the units of g×mil/100 in$^2$×day by $3.937008 \times 10^{-1}$ will convert the units to g×mm/m$^2$×day.

The film used to form the exterior layer 12 may be a single layer film or it may be a multilayer film or a laminate of one or more layers. In addition, if desired additional layers may be adhered or otherwise joined to the film including, but not limited to, fibrous nonwoven webs and other materials. If it is desired that the exterior layer 12 be permeable below with respect to the interior layer 14.

A number of suitable polymers are available from the Dow Chemical Company of Midland, Mich. including, but not limited to, Dow® AFFINITY™ polyolefin plastomers such as Dow® AFFINITY™ PF 1140G POP and ultra-low density polyethylene films such as Dow® ATANE™ ULDPE.

Interior Layer

The interior layer can be made from a wide variety of film-forming polymers provided the resultant layer is permeable to water and/or water vapor. Such breathable films are well known in the art. Examples of suitable polymers include, but are not limited to, polyolefins, polyolefin plastomer polymers (POP), ultra-low density polyethylene (ULDPE), linear low density polyethylene (LLDPE), low density polyethylene (LDPE), styrene-butadiene copolymers, ethylene vinyl acetate (EVA) and very low density polyethylene (VLDPE). Filled and stretched films are also suitable films for the interior layer 14. Such films are widely known in the art. They are typically made by mixing a certain quantity of a filler, such as calcium carbonate, into the film polymer, forming the filled polymer into a film and then stretching the film to make it breathable and able to pass water and water vapor. In addition, apertured films are also suitable for the interior layer 14 and such films are also widely known in art.

A number of suitable film polymers are available from the Dow Chemical Company of Midland, Mich. including, but not limited to, Dow® AFFINITY™ polyolefin plastomers such as Dow® AFFINITY™ PF 1140G POP and ultra-low density polyethylene films such as Dow® ATANE™ ULDPE.

In addition to films, foam materials (such as open-cell foams) may also be used as may fibrous nonwoven webs (such as spunbond webs, meltblown webs, staple fiber webs and combinations of the foregoing) as well as laminates of any or all of the aforementioned films, foams and fibrous nonwoven webs.

Films used to form the interior layer 14 should have a water vapor rate greater than 3.0 g×mil/100 in$^2$×day (1.18 g×mm/m$^2$×day) and desirably between about 3.5 g×mil/100 in$^2$×day (1.38 g×mm/m$^2$×day) and about 6.0 g×mil/100 in$^2$×day (2.36 g×mm/m$^2$×day) in accordance with the aforementioned ASTM test F1249-06 (Reapproved 2011) (at 38° C. and 100 percent relative humidity).

Encapsulating Agent

The purpose of the encapsulating agent 16 is to protect the combination of the carrier material 18 and the active ingredient 20 from premature exposure to water and/or water vapor and replacement of the active ingredient 20 complexed with the carrier material 18 by the water and/or water vapor and to laminate exterior layer 12 and the interior layer 14 together. The time between the original complexing of the active 20 with the carrier 18 and the actual use of the combination within the headspace 34 of the storage unit 30 may be quite long. If this combination is not adequately protected, it can prematurely interact with environmentally present moisture/humidity and begin to lose its effectiveness prior to such time as the carrier/active combination has been loaded into the headspace 34 of a storage unit 30 where it is intended to work.

While it is desirable that the water contained inside the storage unit 30 operate to release the active 20 into the headspace 34 of the storage unit 30 to retard ripening and/or spoilage of the plant material 36 contained in the storage unit 30, this replacement process should not take place prematurely, that is, before the perishable contents 36 and the device 10 are contained in the headspace 34 of the same storage unit 30.

To adequately protect the active ingredient 20, it is desirable that the encapsulating agent 16 have a number of properties including, but not limited to, being non-aqueous, having a low crystallinity and being amorphous. The encapsulating agent 16 must be non-aqueous due to the reactive nature of the active ingredient 20 with water and water vapor. By being amorphous and having a low crystallinity, the encapsulating agent 16 is sufficiently closed to protect the active from water and moisture but also sufficiently open and porous so the structure of the encapsulating agent 16 will permit access to the active ingredient, especially when the device 10 is handled and transported as well as when the device 10 is manipulated by contact with the plant material 36 contained within the headspace 34. Suitable encapsulating agents are desirably semi-solid at room temperature and should have a melting point less than about 80° C. and desirably less than about 50° C. Most typically, the melting point of the encapsulating agent 16 will range between of about 40° C. and about 80° C.

It is also desirable that the encapsulating agent 16 have a glass transition temperature (Tg) of between about minus 200° C. and about 20° C. and more desirably between about minus 30° C. and about 20° C.

Suitable encapsulating agents may include, for example, waxes including animal waxes, vegetable waxes, mineral waxes and synthetic waxes. Exemplary waxes include, but are not limited to, bayberry wax and beeswax. Other suitable materials include petrolatum, stearyl dimethicone, stearyl trimethicone, polyethylene, ethylene-alpha olefin copolymers, ethylene homopolymers, C18-C45 olefins and poly alpha olefins. Commercially available ethylene homopolymers include Petrolite™ EP copolymers from Baker Hughes Inc. of Sugar Land Tex. and poly alpha olefins such as Vybar™ polymers also from Baker Hughes Inc.

Carrier Material

The carrier material 18 should be hydrophobic and water insoluble and, if necessary, be able to complex with the active ingredient. For complexing to occur, a carrier (or host), is used to stabilize an inherent unstable or volatile active (or guest) by forming a stable "carrier/active" inclusion complex (or guest-host complex). The inclusion complex allows the active to remain stable at ambient conditions until a specific stimulus is provided that will trigger the release of the active from the carrier. In the specific instance, the stimulus which allows the active to be released from the complex is water vapor. In one embodiment of the present invention, the host can be cyclodextrin and the guest is the 1-MCP.

One measure of whether a material is hydrophobic is its contact angle which should be at least 90°. One suitable instrument for measuring contact angles is a Rame-Hart model number 200 Contact Angle Goniometer equipped with a Leica APO lens and a Sony 3CCD exwave HAD camera which is available from the Rame-Hart Instrument Company of Mountain Lakes, N.J. The contact angle can be measured by producing a drop of liquid on a solid. The angle formed between the solid/liquid interface and the liquid/vapor interface is referred to as the contact angle. The most common method for measurement involves looking at the profile of the drop and measuring two-dimensionally the angle formed between the solid and the drop profile with the vertex at the three-phase line. It is also desirable for the carrier to be water insoluble. For purposes of the present invention, the water insolubility should be less than or equal to 0.2 grams per 100 milliliters of water at 20° C.

One particularly well-suited carrier material 18 is a cyclodextrin (also referred to herein as "CD") which has been found to complex very well with the active ingredients 20 including 1-MCP. Suitable cyclodextrin compounds include compounds derived from cyclodextrins containing from six to twelve glucose units, including without limitation alpha-cyclodextrins (6 glucose units arranged in a ring), beta-cyclodextrins (7 glucose units arranged in a ring), and gamma-cyclodextrins (8 glucose units arranged in a ring). It has been found, however, that alpha cyclodextrin is the preferred carrier material with respect to the petrolatum encapsulating agent due to the size exclusion effect which precludes the beta and higher glucose-containing units from readily accepting the petrolatum and allowing the encapsulating agent to migrate inside the cyclodextrin. The coupling and configuration of the glucose units causes the cyclodextrins to have a conical molecular structure with a hollow interior lined by hydrogen atoms and glycosidic bridging oxygen atoms.

The cyclodextrin compound should be capable of complexing with the active ingredient 20 and being coated with the encapsulating agent 16 to prevent premature exposure to water and/or water vapor which could prematurely release of the active ingredient 20 from the carrier material 18. Suitable cyclodextrin compounds include methacryloyl-R-cyclodextrins, where R is an alkyl group having 2-20 carbon atoms, desirably 4 to 10 carbon atoms; acryloyl-R-cyclodextrins, where R is an alkyl group having 1 to 20 carbon atoms, desirably 4 to 10 carbon atoms; alkenyl succinylated cyclodextrins, where the alkenyl group has 2 to 20 carbon atoms, desirably 4 to 10 carbon atoms; and the like. The cyclodextrin compound may have a degree of substitution ranging from about 0.1 to about 7. Particularly suitable cyclodextrin compounds include methacryloyl-beta-cyclodextrins, which is a cyclodextrin derivative having an attached methacryloyl moiety that is polymerizable. Polymerization of the methacryloyl-beta-cyclodextrin can be achieved via a radical propagation mechanism and using common chemical or radiation initiation techniques. One presently preferred cyclodextrin compound is 2-hydroxy-3-methylacryloyloxy-propyl-beta cyclodextrin.

Active Ingredient

The purpose of the active ingredient is to help retard plant spoilage and, in particular, plant spoilage associated with exposure of the plant material to ethylene gas. Most typically during plant material transport and storage, the source of the ethylene gas is the plant material, itself. Many chemical compounds have been identified as useful in the retardation of plant material spoilage. There are several different ways such chemicals work. Some chemical compounds are referred to as "ethylene inhibitors" while others are referred to as "ethylene scavengers". For a more detailed explanation of how ethylene inhibitors work see Schotsmans, W. C.; Prange, R. K.; Binder, B. M. In Horticultural Reviews; Janick, J., Ed.; John Wiley and Sons: New Jersey, 2009; Vol. 35, pp 263-313 which is incorporated herein by reference in its entirety and the previously mentioned Tze et al. article. Also see "Ethylene: The Ripening Hormone" by Sylvia Blankenship published by the Washing State University Tree Fruit Research and Extension Center, Nov. 12, 2012 (http://postharvest.tfrec.wsu.edu/pages/PC2000F) which is incorporated herein by reference in its entirety.

Examples of such inhibitors include, but are not limited to, carbon dioxide, silver thiosulfate, cyclopropene, cyclooctene, cyclooctadiene and 1-methyl cyclopropene. In one of the embodiments of the present invention the active ingredient 20 is 1-MCP. When the water and/or water vapor contained in the headspace 34 of the storage unit 30 comes in contact with the carrier material 18, the water/water vapor replaces the complexed active ingredient 20, which is this embodiment is 1-MCP, from the carrier material 18 (which in this case is cyclodextrin) and the 1-MCP is released into the headspace 34 of the storage unit 30. The 1-MCP contacts the plant material 36 and binds with the ethylene plant receptors in the plant material. See, for example, US Patent Application No. 2006/0154822 to Toivonen et al. which is incorporated herein by reference in its entirety and the aforementioned article by Tze et al.

EXPERIMENTAL SECTION

Analytical Test Method

Samples were placed into a clean 250 mL serum bottle with TEFLON® faced silicone septa at time zero ($t_0$). The serum bottle was maintained at room temperature (about 20° C.) during the indicated test interval. At the indicated sampling interval, the serum bottle headspace was sampled by removing 1 mL of gas from the sample bottle. The 1-butene headspace concentration surrounding the test film was quantified using gas chromatography of the 1 mL gas sample.

A gas chromatograph (HP 5890, obtained from the Hewlett Packard Company of Palo Alto, Calif.) operated with flame ionization detection (FID), a six-port heated sampling valve with 250 µL it sampling loop and data collection software (HP ChemStation A06.03-509) was used to measure the 1-butene headspace concentration. Static headspace concentration was determined in test samples using a five point 1-butene calibration curve measured in µL of 1-butene per 250 mL bottle volume and presented as µL/L, or parts per million (vol/vol). Sampling of the serum bottles was accomplished directly through a Valco Instrument six port manual gas sampling valve (Valco #DC6WE, obtained from Valco Instruments Company, Inc. of Houston, Tex.) with 250 µL sampling loop interface directly to a RTx-5 GC column, 30 m×0.25 mm I.D., 0.25 film (obtained from Restek, Inc., of Bellefonte, Pa.). The GC operating conditions are shown in Table 1.

TABLE 1

HP 5890GC Operating Conditions

| | Set Point |
|---|---|
| Zone Temperatures: | |
| Six port valve | 120° C. |
| Detector (FID) | 150° C. |
| Oven zone: | 30° C. |
| Equilibration Time | 0.0 min. |
| Oven Program: | |
| Isothermal Temp: | 150° C. |
| Initial Time (min): | 1.20 |
| Run Time (min): | 1.20 |

The 1-butene working standard was prepared by diluting 10 mL of 99.0% pure 1-butene gas (Scotty Gas #BUTENEO1, obtained from the Sigma Aldrich Corporation of St. Louis, Mo.) in a TEDLAR® gas sampling bag containing 1 liter of air. The 1-butene working standard concentration was 10,226 µL/L (PPM).

Calibration standards were prepared at five concentration levels by injecting via a 250 µL gas tight syringe (Hamilton Gastight® #1725) 50, 100, 200, 300 and 400 µL of the working standard into 250 mL the serum bottles fitted with Teflon® faced silicone septa. ChemStation software was used to calculate a 1-butene response factor using a linear regression equation. The 1-butene standard curve correlation coefficient was 0.999.

EXAMPLE 1

An inclusion complex of 1-butene and α-cyclodextrin was formed using the technique described by Neoh, T. L. et al., *J. Agric. Food Chem.* 2007, 55, 11020-11026 for forming 1-MCP/c/1-MCP, except that 1-butene (99.0% pure, obtained from Scott Specialty Gases of Plumsteadville, Pa.) was bubbled through a saturated α-cyclodextrin solution instead of 1-MCP. A precipitate formed which was collected by filtering through a 10 micron fitted filter and dried at ambient temperature at 0.1 mm Hg for about 24 hours. The precipitate was termed "1-butene/c/a-CD."

The 1-butene/c/a-CD was analyzed by adding 100 mg of the collected and dried precipitate to a 250 mL glass bottle equipped with a septum cap, taking care to ensure that no powder adhered to the walls of the bottle. After about 1 hour, 1 mL of headspace gas was sampled by GC using the GC technique described above. No measurable concentration of 1-butene was detected. Then 3 mL of water was injected into the bottle through the septum, and the bottle was placed on a mechanical shaker and mixed vigorously for about 1 hour. Then 250 µL of the headspace gas was removed and added to an empty 250 mL bottle equipped with a septum cap, wherein the interior of the bottle was purged with nitrogen gas.

The headspace concentration of 1-butene was quantified in the second bottle using gas chromatography by removing 250 µL of gas from the 250 mL bottle using the GC method described above, further wherein the FID detector was previously calibrated, using the 1-butene calibration standards described above, with a 6-point 1-butene calibration curve. Employing this method, the yield of complexed 1-butene/c/a-CD was found to be 94.5%.

EXAMPLE 2

A cyclodextrin composition was applied to a continuously moving flexible web using flexographic printing methodology. A petrolatum composition was formed by immersing a container having a known weight of petrolatum (VASELINE®, melting point 38°-56° C., obtained from Sigma Aldrich Corporation of St. Louis, Mo.) in a water bath at 70° C. until liquified, and mechanically dispersing 4 wt % 1-butene/c/a-CD into the liquefied petrolatum using low shear mixing. The mixture is referred to as Composition 1.

Flexographic printing was carried out using a narrow web rotary printing press (340 mm wide flexographic press obtained from Gallus Inc. of Philadelphia, Pa.). Flexible plates made of engineered photopolymer and having a raised discontinuous diamond relief pattern covering 40% of the plate surface area were adhered to the plate cylinder. The film substrate used for printing was a high barrier film (EXXON MOBIL® BICOR® 210 ASB-X, acrylic and PVdC coated oriented polypropylene, 33 cm wide, obtained from the EXXON MOBIL® Corporation of Irving, Tex.). The fountain trough was loaded with Composition 1. Hot air was blown over the fountain roll to keep Composition 1 liquified. The liquified Composition 1 was applied to the photopolymer plate using a 300 lines per inch (118 lines/cm, 8.35 bcm) anilox roll. The printing press was run at 100 to 150 ft/min (30.5 to 45.7 m/min). The printed Composition 1 was then 'hard-set' using a chill roll is filled with dry ice pellets. Then the entire web surface was coated inline with a UV lamination adhesive (RAAL00160/1060DHV UV/EB Curable Adhesive, obtained from ACTEGA WIT, Inc. of Lincolnton, N.C.) coated via flexo printing, using a 500 lines/in (197 lines/cm, 5.02 bcm) anilox roll before joining a second substrate to the adhesive. The second substrate was a 1 mil (25.4 µm) thick, low density polyethylene (LDPE) web (MI=1.8 g/10 min, density 0.921 g/ml, Vicat sotening point 100° C.) which was applied at a nip, and radiation curing of the adhesive was carried out using UV lamps mounted immediately after the nip point to prevent separation or air pockets in the laminated film. Curing was accomplished with a 300 watt/inch lamp. The completed Treated Laminate 1, a treated laminate containing Composition 1 printed in a diamond pattern, was wound up.

In this manner, Composition 1 was disposed between the two substrate layers of Treated Laminate 1, wherein direct substrate-adhesive-substrate contact in the interstitial areas provided by the diamond pattern effectively isolated Composition 1 into "islands". The isolated islands of the cyclodextrin composition provide for ease of windup, storage, and use. Further, when placed in a container having an item of produce also contained therein, Composition 1 will not contact the produce directly. No petrolatum can contact with the packaged food, and no petrolatum migration is possible.

EXAMPLE 3

Three 10 cm×30.5 cm rectangular samples were cut from Treated Laminate 1. Each sample was loosely rolled up and placed into a separate clean 250 mL bottle for testing according to the Analytical Test Method outlined above. Each bottle was injected with 50 µL of deionized water at $t_0$. Care was taken so that the liquid water did not directly contact the film. Bottle headspace was analyzed for 1-butene at four time periods: 2, 22, 44, and 72 hours after the injection of water, using the GC technique of Example 1. The average headspace concentration of 1-butene and standard deviation for each of the three samples are tabulated in Table 2. The results show that greater amounts of 1-butene were released into the headspace from the laminated film substrate with increasing time.

TABLE 2

Amount of 1-butene released as a function of time.

| Sample | 2 hr 1-Butene ppm | 22 hr 1-Butene ppm | 44 hr 1-Butene ppm | 72 hr 1-Butene ppm |
|---|---|---|---|---|
| A | 0.54 | 17.3 | 20.2 | 19.9 |
| B | 0.49 | 16.3 | 18.2 | 17.9 |
| C | 0.53 | 14.9 | 18.0 | 18.1 |
| Ave. | 0.52 | 16.2 | 18.8 | 18.6 |
| Stdev | 0.03 | 1.2 | 1.2 | 1.1 |

EXAMPLE 4

The α-cyclodextrin was complexed with from 1.0 to 2.25 weight percent 1-butene based upon the weight of the combined 1-butene and α-cyclodextrin. A mixture of 10 weight percent α-cyclodextrin and 90 weight percent petrolatum were mixed in a beaker. The beaker was then placed on a hot plate at 50° C. for about 30 minutes and stirred until the petrolatum melted. A clear and homogeneous dispersion was obtained. The dispersion was then applied to a polyethylene film to an add-on of about 50 weight percent, based upon the weight of the film, via a Meyer rod (#20) to produce a thin coating. Finally a second polyethylene film was placed on top of the coating in such a way that the alpha-cyclodextrin/1-butene/petrolatum coating was sandwiched between and laminated the two polyethylene films.

Two samples as described above were prepared and then tested to determine the level of release of the 1-butene from the device. Two inch by eight inch (5.1×20.3 centimeter) samples of the material were cut and placed in separate 250 milliliter (mL) bottles each of which was humidified with 100 microliters of water and each bottle was sealed with a silicone septa seal. The bottles were maintained at a temperature of 20° C. throughout the testing cycle. Samplings of the environment within each bottle were done at zero hours and subsequently at one, two, four and sixteen hours. The samples were subjected to gas chromatography to measure the level of 1-butene released into the closed environment of the bottles. The amounts of measured 1-butene in parts per million (PPM) for the two samples (Sample A and Sample B) are set forth below in Table 3.

TABLE 3

Amount of 1-butene released as a function of time.

| Sample | Hour | 1-Butene (ppm) |
|---|---|---|
| A | 0 | 0.22 |
| A | 1 | 54.76 |
| A | 2 | 110.63 |
| A | 4 | 179.73 |
| A | 16 | 415.80 |
| B | 0 | 0.44 |
| B | 1 | 35.26 |
| B | 2 | 67.89 |
| B | 4 | 114.60 |
| B | 16 | 307.26 |

As can be seen from the data, despite being encapsulated in petrolatum, the moisture vapor within the sealed environment was able to access the 1-butene complexed with the alpha-cyclodextrin and cause the 1-butene to be released into the closed environment thereby simulating the headspace of a sealed package as would contain plant material such as fruits and vegetables to thereby retard the ripening and degradation of the stored plant material.

This method can easily be practiced commercially on a film food packaging line where an α-cyclodextrin/1-MCP complex is formulated in petrolatum and applied via slot die while sandwiched between two film layers, one of both of which are breathable. The film layers can have different thicknesses and water vapor transmission rates to allow for moisture access to the alpha-cyclodextrin/1-MCP complex which can subsequently trigger the release of 1-MCP in the headspace of the storage unit containing fresh cut fruits and vegetables.

The invention illustratively disclosed herein can be suitably practiced in the absence of any element which is not specifically disclosed herein. While the invention is susceptible to various modifications and alternative forms, specifics thereof have been shown by way of examples, and are described in detail. It should be understood, however, that the invention is not limited to the particular embodiments described. On the contrary, the intention is to cover modifications, equivalents, and alternatives falling within the spirit and scope of the invention. In various embodiments, the invention suitably comprises, consists essentially of, or consists of the elements described herein and claimed according to the claims.

The invention claimed is:

1. A method of making a treated substrate, the method comprising
   heating the composition to a temperature between 60° C. and 80° C., the composition consisting essentially of
      a cyclodextrin inclusion complex comprising a cyclodextrin compound and an olefinic inhibitor; and
      a carrier comprising petrolatum or a petrolatum-like material, wherein the carrier has a melting transition onset between about 23°C and 40°C, and solubility in water of less than 1 wt % at 25°C; and
   disposing the heated composition on a first substrate using a flexographic printing press.

2. The method of claim 1 further comprising cooling the treated substrate, wherein the cooling is accomplished using a chill roll on the flexographic printing press.

3. The method of claim 1 wherein the disposing comprises a discontinuous printed pattern such that the treated substrate comprises 50% or less of the available substrate surface area having the composition disposed thereon.

4. The method of claim 1 further comprising contacting the composition with a second substrate after the disposing.

5. The method of claim 4 wherein an adhesive is disposed between the first substrate and the second substrate.

* * * * *

UNITED STATES PATENT AND TRADEMARK OFFICE
CERTIFICATE OF CORRECTION

PATENT NO. : 9,320,288 B2
APPLICATION NO. : 14/094416
DATED : April 26, 2016
INVENTOR(S) : Willard E. Wood et al.

It is certified that error appears in the above-identified patent and that said Letters Patent is hereby corrected as shown below:

In the Specification

At column 32, line 44:
"about 0° C. and 2° C."
should read:
--about 0° C. and 20° C.--

At column 42, line 53:
"with 250 µL it sampling loop"
should read:
--with 250 µL sampling loop--

In the Claims

At column 46, line 38 (Claim 1, line 3):
"heating the composition"
should read:
--heating a composition--

Signed and Sealed this
Nineteenth Day of July, 2016

Michelle K. Lee
*Director of the United States Patent and Trademark Office*